(12) United States Patent
Yoshida et al.

(10) Patent No.: US 11,914,151 B2
(45) Date of Patent: Feb. 27, 2024

(54) OPTICAL DEVICE, METHOD OF DETECTING DEGREE OF INCLINATION OF THREE-DIMENSIONAL OBJECT, AND LINE-OF-SIGHT DETECTION METHOD

(71) Applicants: Saori Yoshida, Miyagi (JP); Suguru Sangu, Kanagawa (JP)

(72) Inventors: Saori Yoshida, Miyagi (JP); Suguru Sangu, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 6 days.

(21) Appl. No.: 17/643,641

(22) Filed: Dec. 10, 2021

(65) Prior Publication Data

US 2022/0221722 A1 Jul. 14, 2022

(30) Foreign Application Priority Data

Jan. 13, 2021 (JP) ................................. 2021-003521

(51) Int. Cl.
  *G02B 27/01* (2006.01)
  *G02B 27/00* (2006.01)
  *G01C 3/02* (2006.01)

(52) U.S. Cl.
  CPC ........... *G02B 27/0172* (2013.01); *G01C 3/02* (2013.01); *G02B 27/0093* (2013.01); *G02B 2027/014* (2013.01); *G02B 2027/0178* (2013.01)

(58) Field of Classification Search
  CPC ........... G02B 27/0172; G02B 27/0093; G02B 2027/014; G02B 2027/0178; G01C 3/02; A61B 3/113
  See application file for complete search history.

(56) References Cited

U.S. PATENT DOCUMENTS

| | | | |
|---|---|---|---|
| 10,908,683 B2* | 2/2021 | Sarkar | G02B 27/0093 |
| 11,307,405 B2* | 4/2022 | Katsuyama | G09G 3/02 |
| 2006/0262398 A1 | 11/2006 | Sangu et al. | |
| 2010/0060551 A1* | 3/2010 | Sugiyama | G02B 26/06 353/31 |
| 2019/0049731 A1* | 2/2019 | Knuettel | G03H 1/2294 |
| 2020/0035009 A1* | 1/2020 | Comer | G06F 18/23213 |
| 2020/0174564 A1 | 6/2020 | Sangu et al. | |
| 2020/0285058 A1 | 9/2020 | Sangu et al. | |
| 2020/0393896 A1* | 12/2020 | Li | G06F 3/013 |
| 2023/0037329 A1* | 2/2023 | Erkelens | G02B 27/0172 |

FOREIGN PATENT DOCUMENTS

| | | |
|---|---|---|
| JP | 4-146720 | 5/1992 |
| JP | 2020-087200 | 6/2020 |

* cited by examiner

*Primary Examiner* — Bryan Earles
(74) *Attorney, Agent, or Firm* — IPUSA, PLLC

(57) ABSTRACT

An optical device, a method of detecting inclination of a three-dimensional object, and a method of detecting a line-of-sight. The optical device includes a light source configured to irradiate an object with light, a detector configured to detect a position of the light reflected by the object, and circuitry configured to output data of a degree of inclination of the object obtained based on the position of the light and a prescribed parameter, and change the prescribed parameter based on the position of the light. The above methods include irradiating an object with light, detecting a position of the light reflected by the object, outputting data of a degree of inclination of the object obtained based on the position of the light and a prescribed parameter, and changing the prescribed parameter based on the position of the light.

14 Claims, 13 Drawing Sheets

OPTICAL DEVICE, METHOD OF DETECTING DEGREE OF INCLINATION OF THREE-DIMENSIONAL OBJECT, AND LINE-OF-SIGHT DETECTION METHOD

CROSS-REFERENCE TO RELATED APPLICATION

This patent application is based on and claims priority pursuant to 35 U.S.C. § 119(a) to Japanese Patent Application No. 2021-003521, filed on Jan. 13, 2021, in the Japan Patent Office, the entire disclosure of which is hereby incorporated by reference herein.

BACKGROUND

Technical Field

Embodiments of the present disclosure relate to an optical device, a line-of-sight detection device, a retinal projection display device, a head-mounted display device, an optometric device, a method of detecting the degree of inclination of a three-dimensional object, and a line-of-sight detection method.

Background Art

Optical devices are known in the art that optically detect the degree of inclination of an object such as an eye.

For example, mechanisms of such optical devices to irradiate an eye with light and detect the movement of the eye based on the light reflected by the eye are known in the art.

SUMMARY

Embodiments of the present disclosure described herein provide an optical device, a method of detecting inclination of a three-dimensional object, and a method of detecting a line-of-sight. The optical device includes a light source configured to irradiate an object with light, a detector configured to detect a position of the light reflected by the object, and circuitry configured to output data of a degree of inclination of the object obtained based on the position of the light and a prescribed parameter, and change the prescribed parameter based on the position of the light. The above methods include irradiating an object with light, detecting a position of the light reflected by the object, outputting data of a degree of inclination of the object obtained based on the position of the light and a prescribed parameter, and changing the prescribed parameter based on the position of the light.

BRIEF DESCRIPTION OF THE DRAWINGS

A more complete appreciation of embodiments and the many attendant advantages thereof will be readily obtained as the same becomes better understood by reference to the following detailed description when considered in connection with the accompanying drawings.

FIG. 2A illustrates a case in which the eye is not inclined and FIG. 2B illustrates a case in which the eye is inclined.

FIG. 9A illustrates a case in which the number of detection values is five, according to an embodiment of the present disclosure.

FIG. 9B illustrates a case in which the number of detection values is ten, according to an embodiment of the present disclosure.

FIG. 9C illustrates a case in which the number of detection values is fifteen, according to an embodiment of the present disclosure.

Figure 1:
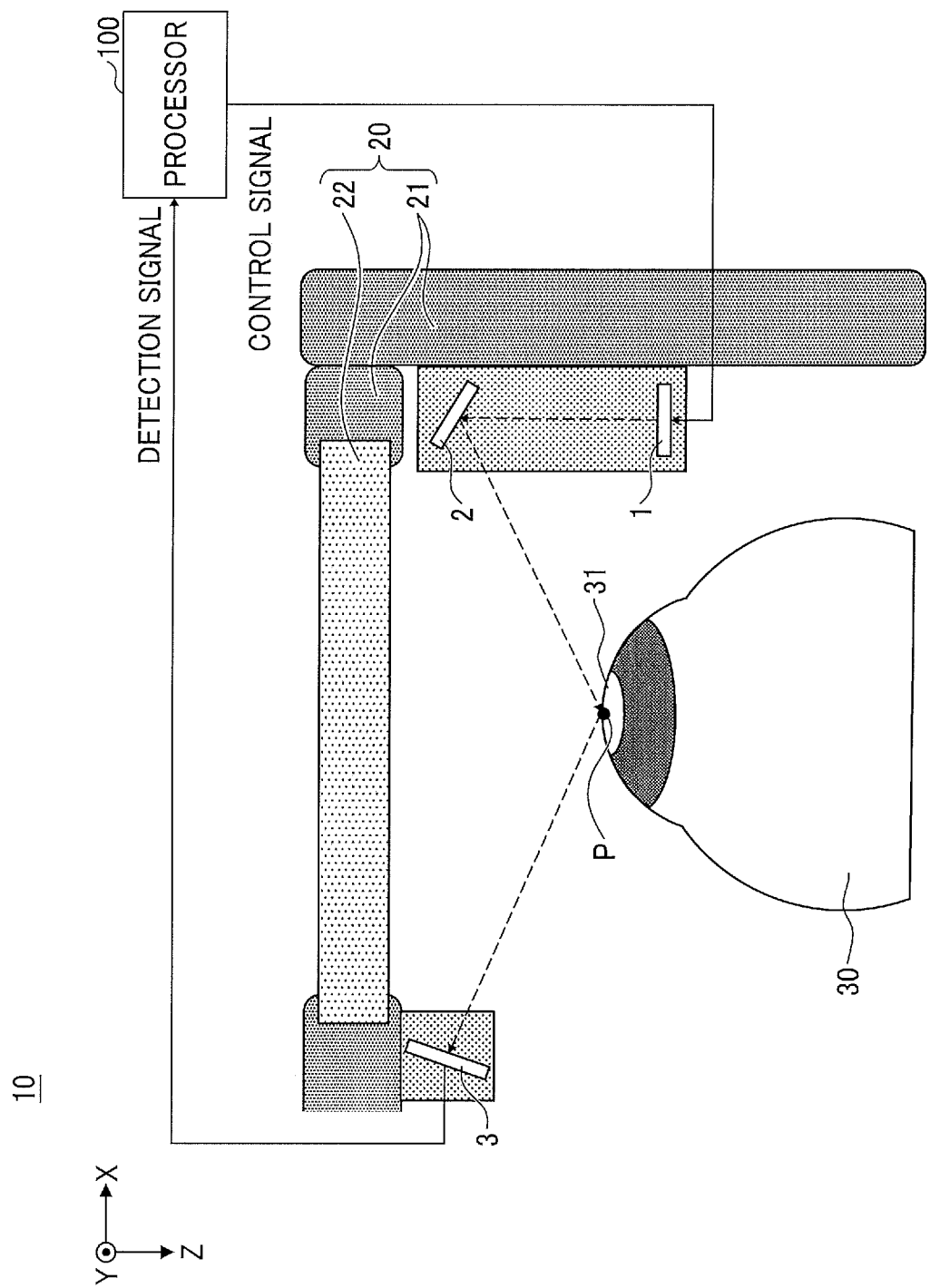
FIG. 1 is a diagram illustrating a configuration of a line-of-sight detection device according to a first embodiment of the present disclosure.

The accompanying drawings are intended to depict embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

In the following description, illustrative embodiments will be described with reference to acts and symbolic representations of operations (e.g., in the form of flowcharts) that may be implemented as program modules or functional processes including routines, programs, objects, components, data structures, etc., that perform particular tasks or implement particular abstract data types and may be implemented using existing hardware at existing network elements or control nodes. Such existing hardware may include one or more central processing units (CPUs), digital signal processors (DSPs), application-specific integrated circuits (ASICs), field-programmable gate arrays (FPGAs), computers or the like. These terms may be collectively referred to as processors.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Embodiments of the present disclosure are described below with reference to the accompanying drawings. In the drawings, like reference signs denote like elements, and overlapping description may be omitted.

An optical device according to embodiments of the present disclosure is described below to implement the technical ideas, and no limitation is indicated to the embodiments of the present disclosure given below. For example, the shape of components, the relative positions of the arranged components, and the values of parameters are given by way of example in the following description, and the scope of the present disclosure is not limited thereto unless particularly specified. The size of these elements or the relative position of these elements may be exaggerated for purposes of illustration in the drawings.

The optical device according to the present embodiment detects the inclination of an object. The object according to the present embodiment is, for example, a human eye, and the optical device according to the present embodiment is a line-of-sight detection device used to detect a line-of-vision direction that is the direction in which someone is looking. As the eye is inclined towards the line of vision or line of sight of a subject, the line-of-sight detection device detects the inclination of the eye. As a result, the line-of-vision direction can be detected. In other words, the inclination of the eye indicates the angle of rotation of the eye.

For example, the information about the line-of-vision direction detected by the line-of-sight detection device is used by eye tracking devices or optometric devices. Alternatively, the information about the line-of-vision direction is used to correct the position of the projected image or the image data according to the inclination of the eye when an image is projected onto a retina or the like by, for example, a retinal projection display device and a head-mounted display (HMD).

The optical device according to the present embodiment irradiates an object with light, and detects the position of the light reflected by the object. As a result, the data about the inclination of the object that is obtained based on the position of the light and prescribed parameters is output. In the present embodiment, the parameters refer to the information used when the information about the degree of inclination of the object is obtained by computation from the detection value of the position of light. The parameters include, for example, the information about the size or shape of the eye 30 and the information about the position of the center of rotation of the eye 30.

For example, fixed parameters consistent with the size, the shape, and the position of the center of rotation of a typical or average eye may steadily be used as the parameters. However, due to variations among individuals, the size or shape of the eye or shape of an eye may greatly deviate from typical parameters, or the position at which the optical device is disposed may greatly deviate from a predetermined position. In such cases, the light that is reflected by an object may greatly deviate from a desired position. As a result, the use of fixed parameters may increase the detection error of the inclination of the object.

In the present embodiment, the above parameters are changed based on the position of the light reflected by the object such as the eye. For example, some of a plurality of detection values obtained as a result of detection of the position of the light reflected by the object may be used to change the above parameters based on the position of the center of gravity of the detection values making up the cluster and the width of change in the detection values making up the cluster. A cluster indicates a set of detection values including a plurality of detection values.

As known in the art, human eyes constantly perform, for example, unconscious micro-movement called involuntary eye movement during fixation. The position of the light that is reflected by the eye changes in a distribution that varies depending on the characteristics of the involuntary eye movement during fixation. Further, the characteristic of the involuntary eye movement during fixation varies depending on, for example, variations among individuals in the size or shape of the eye and the displacements in the position at which the optical device is disposed.

Accordingly, in view of some of a plurality of detection values obtained as a result of detection of the position of the light, the position of the center of gravity of the detection values making up the cluster and the width of change in the detection values making up the cluster may be used to extract the amount of characteristic that indicates the characteristics of involuntary eye movement during fixation.

As the parameters (R1, R2, and d) are changed based on the extracted amount of characteristic, the influence of, for example, a deviation in the size or shape of the eye and a deviation in the installation position of the optical device can be compensated for. Accordingly, the detection error can be reduced even when the light reflected by the object deviates significantly.

In the following description, the line-of-sight detection device according to the present embodiment, which is mounted on an spectacle-shaped supporting structure and detects, as a line-of-vision direction, the degree of inclination of an eye of a person wearing the spectacle-shaped supporting structure, serves as an optical device. The human eye according to the present embodiment serves as an object. The line-of-vision direction according to the present embodiment indicates the degree of inclination of the object. In the present embodiment, the description is given in view of the right eye of human, but the same applies to the left eye of human. Alternatively, a pair of line-of-sight detection devices according to the present embodiment may be applied to both eyes, respectively.

For the sake of explanatory convenience, in the following description described with reference to the accompanying drawings, a horizontal direction orthogonal to a vertical direction is referred to as an X-axis direction, and the vertical direction is referred to as a Y-axis direction. Further, a direction orthogonal to both the X-axis direction and the Y-axis direction is referred to as a Z-axis direction. The Z-axis direction approximately match the plus-sight direction of the eye. However, the position and orientation of the line-of-sight detection device are not limited to the above assumptions or the like, and the line-of-sight detection device can be disposed at any position and can be disposed in any orientation.

First Embodiment

FIG. 1 is a diagram illustrating a configuration of a line-of-sight detection device 10 according to a first embodiment of the present disclosure.

As illustrated in FIG. 1, the line-of-sight detection device 10 according to the present embodiment includes a vertical-cavity surface-emitting laser (VCSEL) 1, a plane mirror 2, a position sensitive detector (PSD) 3, and a processor 100.

A spectacle-shaped supporting structure 20 includes a spectacle frame 21 and a spectacle lens 22, and the VCSEL 1, the plane mirror 2, and the PSD 3 are attached to the spectacle frame 21. The processor 100 can be disposed at any position. In the present embodiment described with reference to FIG. 1, the processor 100 is arranged outside the spectacle-shaped supporting structure 20. However, no limitation is indicated thereby, and the processor 100 may be arranged inside the spectacle frame 21.

The VCSEL 1 according to the present embodiment serves as a light source that irradiates the eye 30 with a laser beam. The VCSEL 1 includes a plurality of light emitters that are two-dimensionally arranged on an imaginary plane. Each one of multiple light emitters emits a laser beam in a reverse Z-axis direction. The laser beam that is emitted from each one of the multiple light emitters of the VCSEL 1 is an example of the light emitted from the light source. The term "multiple light emitters" is synonymous with a plurality of light-emitting points or a plurality of light-emitting elements.

However, the light source is not limited to a VCSEL as long as the eye 30 can be irradiated with the light emitted from a plurality of light emitters. For example, the light source may be configured by two-dimensionally arranging a plurality of laser diodes (LDs) or semiconductor lasers on a plane or by two-dimensionally arranging a plurality of light-emitting diodes (LEDs) on a plane. Alternatively, the light source may be configured by combining a plurality of types of light sources.

When a plurality of light-emitting units are not used in order to broaden the field of line-of-sight detection as will be described later, the light source may have only one light emitter such as a single laser diode (LD).

The light that is emitted from the light source may be incoherent light or coherent light such as a laser beam. It is even more desirable if a laser beam with directivity because the light can be easily guided to the eye 30.

Alternatively, the light may be continuous wave (CW) light or pulsed light. The wavelength of the light that is emitted from the light source is not particularly limited, but it is more desirable if wavelength of invisible light such as near-infrared light is adopted because such invisible light does not affect or interfere with human visual recognition or visual perception.

The plane mirror 2 according to the present embodiment is a light guide that reflects the laser beam emitted from the VCSEL 1 toward the eye 30 to guide the laser beam to the eye 30. The laser beam that is reflected by the plane mirror 2 is incident on an area of the eye 30 around the pupil 31. The degree of inclination of each one of the VCSEL 1 and the plane mirror 2 is adjusted such that the laser beam is incident at a predetermined angle in the center of the pupil 31 of the eye 30 in a plus-sight state.

However, the light guide is not limited to the plane mirror 2. For example, the light guide may be configured by any one of a convex lens, a microlens array, a concave curved mirror, a hologram diffraction element, a prism array, and a diffraction grating, or may be configured by any combination of these elements. When the light guide is configured by a combination of these elements, the number of elements to be combined may be two or more. As the configuration or structure of the light guide is optimized, for example, the line-of-sight detection field may be broadened, or the size of the line-of-sight detection device 10 may be reduced. Moreover, the load of assembly may be reduced.

It is not always necessary for the line-of-sight detection device 10 to be provided with a light guide, and the laser beam that is emitted from the VCSEL 1 may directly be incident on the eye 30.

The surface of the pupil or cornea of the eye 30 is transparent, and contains moisture. Typically, the surface of the pupil or cornea of the eye 30 has a reflectance of about 2 to 4%. The laser beam that is incident on a point of the eyes 30 near the pupils 31 is reflected by the eye 30 at a point of reflection P on the surface of the pupil, and forms a beam spot on the photo-sensing surfaces of the PSD 3.

The PSD 3 according to the present embodiment serves as a detector that detects the position of the laser beam reflected by the eye 30. The PSD 3 is a two-dimensional optical position sensitive detector that has a photo-sensing surface and four output terminals and outputs a detection signal indicating the position of incident light in two directions orthogonal to each other on the photo-sensing surface. The PSD 3 detects a current value of a laser beam that forms a beam spot on the photo-sensing surface, which varies depending on the distances to an electrode, and outputs a detection signal that varies depending on the ratio between a pair of current values in two directions orthogonal to each other.

The photo-sensing surface is a continuous plane that is not divided into pixels, and includes a resistive film formed on the surface and a pair electrodes arranged in two directions orthogonal to each other. The photoelectric current that is generated at the beam spot position on the photo-sensing surface is divided into four according to the distance to each one of the output terminals. In so doing, the electrical resistance that is caused by the resistive film functions to decrease the electric current to have a smaller value as the distance between the beam spot position and the output terminal becomes longer.

The PSD 3 according to the present embodiment detects, through four terminals, an electrical signal that has passed through the resistive film, and outputs a detection signal that is obtained as a result of electrical post-processing and indicates the position on the photo-sensing surface. Moreover, the PSD 3 according to the present embodiment can convert the current generated as a result of photoelectric conversion into an analog voltage signal, and can output the obtained analog voltage signal as a detection signal through the four terminals. In other words, the PSD 3 obtains the distance to each one of the terminals based on the surface resistivity. As a result, the incident position can be detected.

Instead of the PSD 3, the detector according to the present embodiment may be an image sensor or imaging device including a plurality of pixels. The PSD 3 may be a one-dimensional PSD used to detect a one-dimensional position instead of a two-dimensional PSD used to detect a two-dimensional position of a laser beam on the photo-sensing surface.

However, in such an image sensor, when the light intensity of the received laser beam is small compared with ambient light or environmental light such as sunlight, the accuracy of detection of the position of the laser beam may deteriorate. If the output power of the VCSEL 1 is increased in order to prevent a reduction in accuracy of detection, the light intensity of the laser beam to be emitted and incident on the eye 30 increases, and such an increase in light intensity is undesired in view of safety.

Moreover, in such an image sensor, a detection error due to calculation or computation may occur or the processing load may increase as images are processed to detect positions.

As the PSD 3 is used as a detector, the position can be detected based on the ratio of the current that is divided into several output terminals. Due to such a configuration, the light intensity of the received laser beam has a small influence or impact on the accuracy of position detection. Accordingly, it is not necessary to increase the light intensity of the laser beam to be emitted and incident on the eye 30 in order to reduce the influence caused by ambient light or environmental light. Due to such a configuration, the light intensity of the laser beam that is incident on the eye 30 can be reduced, and such a reduction in light intensity is advantageous in view of safety.

Moreover, as position are detected without performing image processing, detection errors and processing loads that come with or are caused by image processing can be reduced.

Due to the inclination of the eye 30, the position of a beam spot formed on the photo-sensing surface of the PSD 3 by light reflected by the eye 30 changes. The PSD 3 outputs detection signals corresponding to the position of the beam spot to the processor 100.

The processor 100 according to the present embodiment converts the detection signals obtained by the PSD 3 into coordinates, and outputs the information about the line-of-vision direction obtained by performing computation, based on the coordinates indicating the position of the laser beam and predetermined parameters.

In other words, the PSD 3 detects the direction of the normal vector of the point of reflection on the eye 30. As a result, the three dimensional shape of the eye 30 is obtained. The processor 100 can output the information about the degree of inclination of the eye 30, which is obtained as a result of estimating computation, based on the relation between the surface-profile model of the eye 30 and the three-dimensional shape of the eye 30 detected by the PSD 3. Such a surface-profile model of the eye 30 according to the present embodiment serves as the parameters, and includes, for example, the information about the size or shape of the eye 30 and the information about the position of the center of rotation of the eye 30.

In the description of the present embodiment given above with reference to FIG. 1, the spectacle frame 21 is used as a holding member of a component such as the VCSEL 1. However, no limitation is indicated thereby. A component such as the VCSEL 1 may be held on a member such as a cap, a hat, and a head gear that can be worn by a human head in its entirety.

In the present embodiment, the eye 30 performs eye motion such as rotation. Due to such rotation, the eye 30 is inclined. When the direction of the laser beam that is reflected by the eye 30 changes greatly due to the inclination of the eye 30, there may be some cases in which the laser beam is not incident on the photo-sensing surface of the PSD 3. As a result, the PSD 3 may fail to detect the position of the reflected laser beam.

In the present embodiment, the multiple light emitters of the VCSEL 1 are sequentially or selectively changed. By so doing, the laser beam that is reflected by the eye 30 can be prevented from not being incident on the photo-sensing surface of the PSD 3. As a result, even when the eye 30 is significantly inclined, a state in which the laser beam reflected by the eye 30 is incident on the photo-sensing surface of the PSD 3 can be maintained, and the field of line-of-sight detection can be expanded.

Figure 2A:
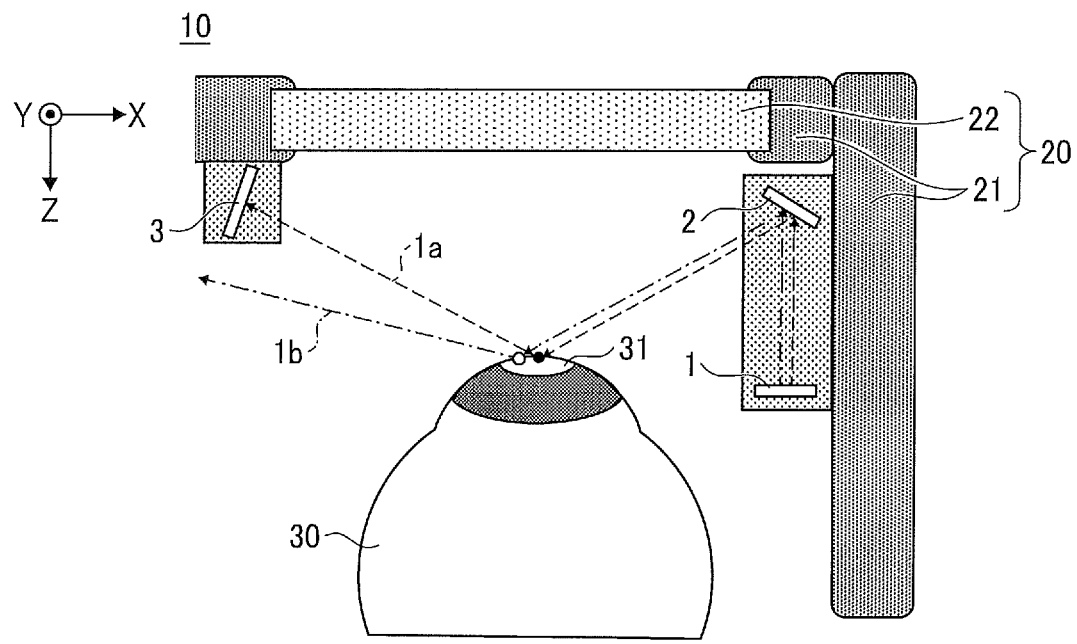
FIG. 2A and FIG. 2B are diagrams each illustrating the relation between the inclination of an eye and the position on a position sensitive detector (PSD) on which a laser beam is incident, according to an embodiment of the present disclosure, where
Figure 2B:
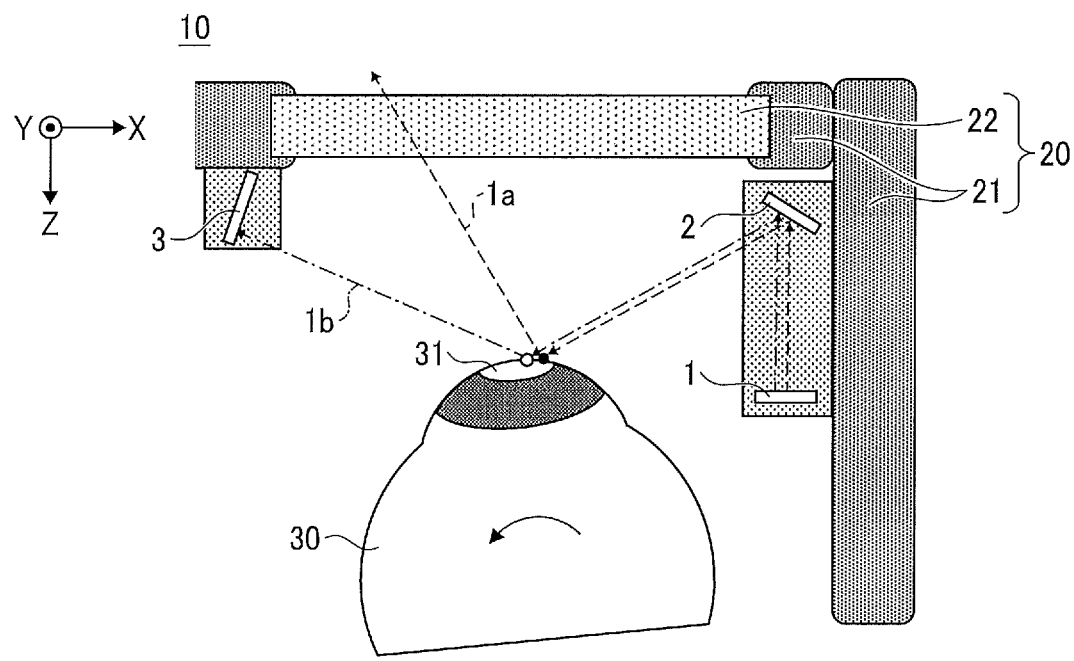

FIG. 2A and FIG. 2B are diagrams each illustrating the relation between the inclination of the eye 30 and the position on the PSD 3 on which a laser beam is incident, according to the present embodiment.

More specifically, FIG. 2A illustrates a plus-sight case in which the eye 30 is not inclined, and FIG. 2B illustrates a case in which the eye 30 is inclined.

FIG. 2A and FIG. 2B illustrate the propagation of the laser beams emitted from two of the multiple light emitters of the VCSEL 1. In FIG. 2A and FIG. 2B, a laser beam 1a that is emitted from one of the light emitters is indicated by a dotted line, and a laser beam 1b that is emitted by another one of the light emitters is indicated by alternate long and short dashed lines.

As illustrated in FIG. 2A, the laser beam 1a is reflected by the eye 30, and then is incident on a point around the center of the photo-sensing surface of the PSD 3. Under such conditions, the PSD 3 can detect changes in the position of the photo-sensing surface on which the laser beam 1a is incident, depending on the degree of inclination of the eye 30, and the line-of-sight detection device 10 can detect the degree of inclination of the eye 30 based on the detection signals of the PSD 3, and can detect the line-of-vision direction.

On the other hand, the laser beam 1b is not incident on the photo-sensing surface of the PSD 3 after the reflection by the eye 30. Under such conditions, the PSD 3 cannot detect the position of the laser beam 1b. As a result, the line-of-sight detection device 10 cannot detect the inclination of the eye 30 based on the signals detected by the PSD 3, and cannot detect the line-of-vision direction.

As illustrated in FIG. 2B, when the eye 30 is significantly inclined, the laser beam 1a is not incident on the photo-sensing surface of the PSD 3 after reflected by the eye 30. Under such conditions, the PSD 3 cannot detect the position of the laser beam 1a. As a result, the line-of-sight detection device 10 cannot detect the degree of inclination of the eye 30, and cannot detect the line-of-vision direction.

On the other hand, the laser beam 1b is reflected by the eye 30, and then is incident on a point around the center of the photo-sensing surface of the PSD 3. Under such conditions, the PSD 3 can detect changes in the position of the photo-sensing surface on which the laser beam 1b is incident, depending on the degree of inclination of the eye 30. Moreover, the line-of-sight detection device 10 can detect the degree of inclination of the eye 30 based on the detection signals of the PSD 3, and can detect the line-of-vision direction.

As described above, with the laser beam emitted by only one light emitter in the VCSEL 1, the inclination of the eye 30 can be detected only in a limited angle range among the inclination angles of the eye 30, and the line-of-vision direction cannot be detected.

In order to handle such a situation, in the present embodiment, the multiple light emitters of the VCSEL 1 are changed according to the degree of inclination of the eye 30 to change the incident angle at which each laser beam is incident on the eye 30.

For example, one of the multiple light emitters of the VCSEL 1 is made emit a laser beam to determine whether or not the PSD 3 outputs any detection signal. When it is determined that no detection signal is output from the PSD 3, a different one of the multiple light emitters of the VCSEL 1 is made to emit light again to determine whether or not the PSD 3 outputs any detection signal. Such an operation is repeated until the PSD 3 finally outputs a detection signal. By so doing, a condition is achieved in which the laser beam reflected by the eye 30 is incident on the photo-sensing surface of the PSD 3.

Moreover, even when the eye 30 is significantly inclined, a condition or state is maintained in which the laser beam reflected by the eye 30 is consistently incident on the photo-sensing surface of the PSD 3. As a result, the degree of inclination of the eyes 30 can be detected based on the detection signals output from the PSD 3, and the field of line-of-sight detection can be increased.

The operation of changing the multiple light emitters of the VCSEL 1 does not necessarily have to be performed in accordance with the eye motion such as inclination. For example, the line-of-sight detection device 10 may cause the multiple light emitters of the VCSEL 1 to sequentially emit a laser beam at predetermined time intervals independently of the eye motion, and may cause the laser beam reflected by the eye 30 to be incident on the photo-sensing surface of the PSD 3 based on the signal detected by the PSD 3 at that time.

In FIG. 2A and FIG. 2B, only the laser beams that are emitted from two light emitters are illustrated for purposes of simplification. However, no limitation is indicated thereby, and the line-of-sight detection device 10 can use a larger number of light emitters provided for the VCSEL 1 according to the eye motion of the eye 30. In such cases, the line-of-sight detection device 10 selects the number of the light emitters of the VCSEL 1 and the positions of the selected light emitters as appropriate, such that the degree of inclination of the eye 30 can appropriately be detected in view of the size of the photo-sensing surface of the PSD 3 and the size of the eye 30.

Figure 3:
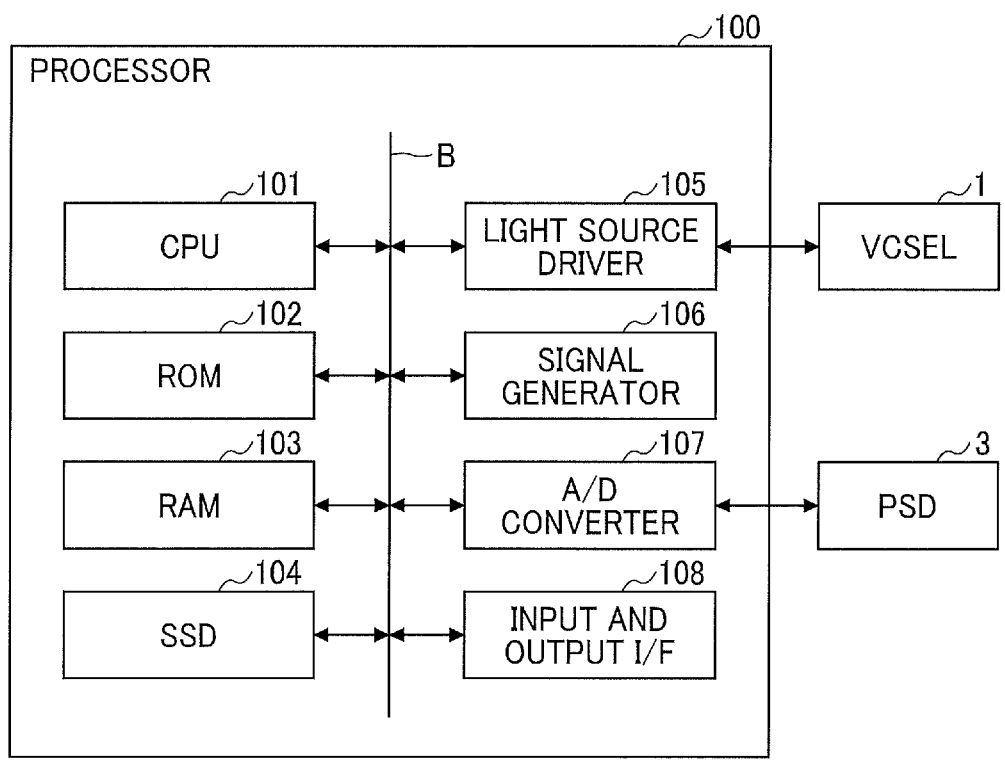
FIG. 3 is a block diagram of a hardware configuration of a processor according to the first embodiment of the present disclosure.

FIG. 3 is a block diagram of a hardware configuration of the processor 100 according to the present embodiment.

As illustrated in FIG. 3, the processor 100 includes a central processing unit (CPU) 101, a read only memory (ROM) 102, a random access memory (RAM) 103, and a solid state drive (SSD) 104. The processor 100 according to the present embodiment includes a light source driver 105, a signal generator 106, an analog-to-digital (A/D) converter 107, and an input and output interface (I/F) 108. These elements of the processor 100 are coupled to each other through a system bus B such that data or signals can be exchanged.

The CPU 101 loads into the RAM 103 a program or data from a storage device such as the ROM 102 and the SSD 104 and performs processes. Accordingly, the controls or functions of the entirety of the processor 100, as will be described later in detail, are implemented. Some of or the entirety of these functions of the CPU 101 may be enabled by electronic circuit such as an application specific integrated circuit (ASIC) and a field-programmable gate array (FPGA).

The ROM 102 is a read-only nonvolatile semiconductor memory or storage device that can store a computer program or data even when the power is switched off. The ROM 102 stores a computer program or data that is executed when the processor 100 starts up, such as a basic input/output system (BIOS), the settings of the operating system (OS), and the settings of the network. The RAM 103 is a volatile semiconductor memory or storage device that temporarily stores data or a computer program.

The SSD 104 is a nonvolatile memory that stores various kinds of data or a program used to execute the processes performed by the processor 100. The SSD 104 may be a hard disk drive (HDD).

The light source driver 105 according to the present embodiment is an electric circuit that is electrically coupled to the VCSEL 1 and outputs a driving voltage to the VCSEL 1 according to the control signals. The light source driver 105 can simultaneously or sequentially drive a plurality of light emitters provided for the VCSEL 1 to emit light.

A rectangular wave, a sine wave, or a voltage waveform having a predetermined waveform can be used as the driving voltage, and the light source driver 105 can change the cycles or frequencies of such a voltage waveform to modulate the cycles of the driving voltage.

The signal generator 106 is an electric circuit that generates an electrical signal having a predetermined cycle. The signal generator 106 may be a multi-channel signal generator that can generate a plurality of electrical signals having different cycles and output the generated electrical signals to a plurality of destination devices in parallel.

The A/D converter 107 is an electric circuit that is electrically coupled to the PSD 3 and is used to convert the analog voltage signal output from the PSD 3 to output a digital voltage signal. The detection value that is obtained by the PSD 3 can be acquired from the digital voltage signal output from the A/D converter 107.

The input and output interface 108 is an interface with an external device such as a personal computer (PC) or video equipment.

First Embodiment

Figure 4:
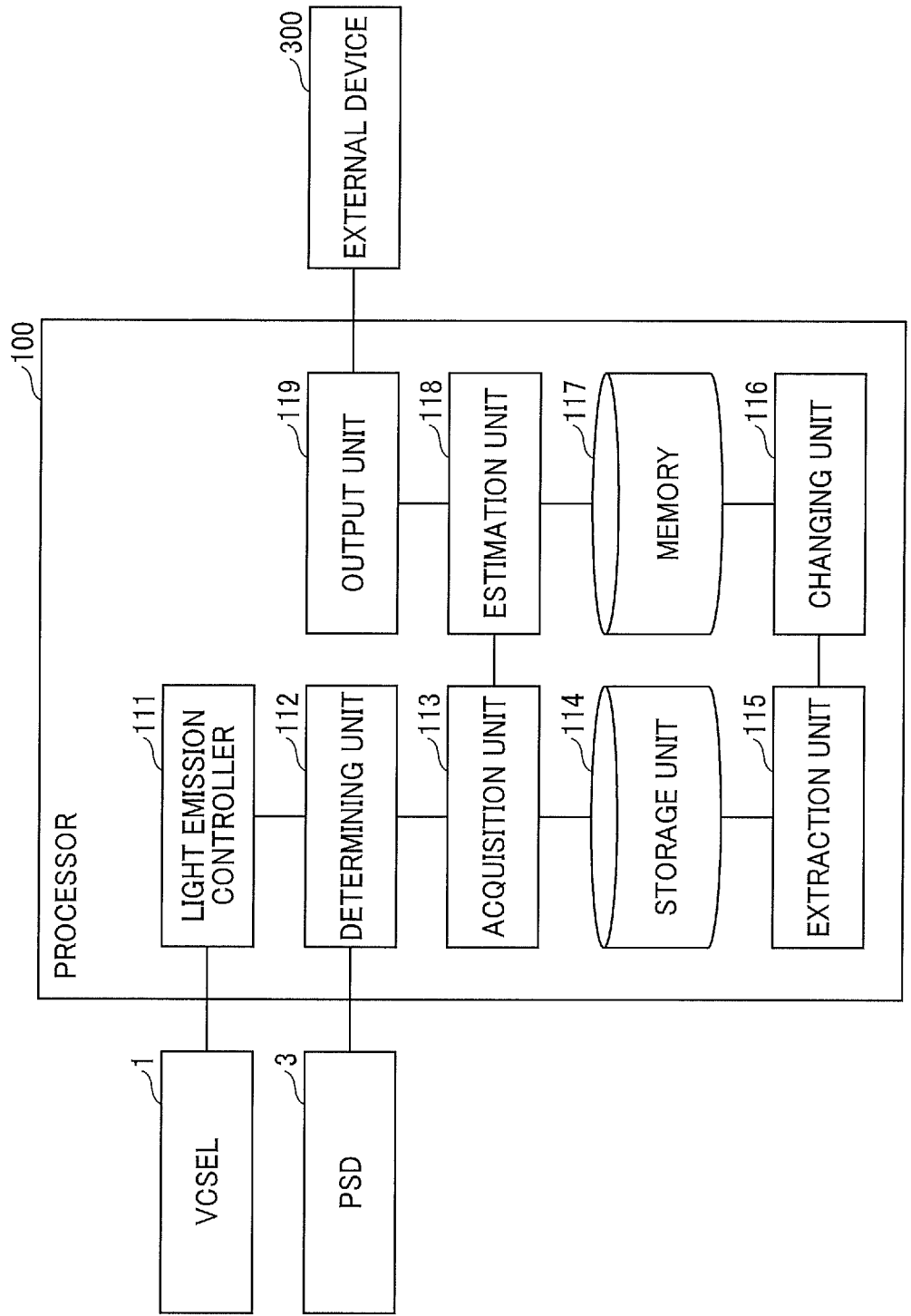
FIG. 4 is a block diagram of a functional configuration of a processor according to the first embodiment of the present disclosure.

FIG. 4 is a block diagram illustrating a functional configuration of the processor 100, according to the present embodiment.

As illustrated in FIG. 4, the processor 100 includes a light emission controller 111, a determining unit 112, an acquisition unit 113, a storage unit 114, an extraction unit 115, a changing unit 116, a storage unit 117, an estimation unit 118, and an output unit 119.

These elements or units are functions implemented by or caused to function by operating some of the elements illustrated in FIG. 3 under the control of the instructions from the CPU 101. Note also that such instructions from the CPU 101 are made in accordance with the program expanded from the ROM 102 to the RAM 103. FIG. 4 schematically illustrates a configuration of the processor 100. However, no limitation is indicated thereby, and the processor 100 may further include other elements or units in addition to those elements or units illustrated in FIG. 4.

The light emission controller 111 and the determining unit 112 may cooperate to cause the laser beam reflected by the eye 30 to be incident on the photo-sensing surface of the PSD 3. More specifically, the light emission controller 111 selects one of the multiple light emitters of the VCSEL 1 to emit light.

The determining unit 112 receives a detection signal output from the PSD 3, and determines whether the laser beam reflected by the eye 30 has already been incident on the photo-sensing surface of the PSD 3. For example, when the voltage or current of the detection signal output from the PSD 3 is equal to or greater than a predetermined threshold, the determination unit 112 determines that the laser beam has already been incident on the photo-sensing surface of the PSD 3. By contrast, when the voltage or current of the detection signal output from the PSD 3 is not equal to or greater than a predetermined threshold, the determination unit 112 determines that the laser beam is not yet incident on the photo-sensing surface of the PSD 3.

When it is determined that the laser beam is not yet incident on the photo-sensing surface of the PSD 3, the light emission controller 111 changes the selected one of the multiple light emitters of the VCSEL 1 to another one of the light emitters to emit light. Then, the light emission controller 111 repeats changing the selected on of the multiple light emitters of the VCSEL 1 until it is determined that the laser beam has already been incident on the photo-sensing surface of the PSD 3. By so doing, the light emission controller 111 and the determining unit 112 can cause the laser beam reflected by the eye 30 to be incident on the photo-sensing surface of the PSD 3.

After the laser beam reflected by the eye 30 is incident on the photo-sensing surface of the PSD 3, the determining unit 112 outputs the signals detected by the PSD 3 to the acquisition unit 113.

The acquisition unit 113 performs analog-to-digital (A/D) conversion on the analog voltage signal that is detected by the PSD 3 and then input through the determining unit 112, to obtain, as a detection value, a digital voltage signal that indicates the position of a laser beam on the photo-sensing surface of the PSD 3. The acquisition unit 113 controls the storage unit 114 to store the obtained detection value.

The storage unit 114 according to the present embodiment sequentially stores the detection values acquired by the acquisition unit 113. For example, the functionality of the storage unit 114 is implemented by the SSD 104.

The extraction unit 115 according to the present embodiment calculates the position of the center of gravity of the detection values making up the cluster and the width of change in the detection values making up the cluster in view of some of the multiple detection values stored in the storage unit 114, to extract the amount of characteristic that indicates the characteristics of involuntary eye movement during fixation. The extraction unit 115 outputs the extracted data indicating the amount of characteristic to the changing unit 116.

The changing unit 116 according to the present embodiment changes the parameters stored in the storage unit 117, based on the amount of characteristic input from the extraction unit 115. The parameters include, for example, the information about the size or shape of the eye and the information about the position of the center of rotation of the eye. The changing unit 116 can refer to, for example, a conversion formula indicating the relation between the amount of characteristic and the multiple parameters, to change each one of the parameters based on the amount of characteristic.

The functions of the extraction unit 115 and the changing unit 116 will be described later in detail with reference to FIG. 6 to FIG. 8.

The estimation unit 118 calculates the degree of inclination of the eye 30 based on the position of the laser beam reflected by the eye 30 and the parameters stored in the storage unit 117, to obtain information about the line-of-vision direction.

The degree of inclination of the eye 30 is calculated using mathematical expression of a linear function or a quadric function. However, the mathematical expression for the calculation is not limited to this, and any mathematical expression may be used as long as the degree of inclination of the eye 30 can be calculated from the incident angle of the laser beam on the eye 30 and the beam spot position on the photo-sensing surface of the PSD 3. In the present embodiment, a quadric function is used as a simple approximate expression.

A surface-profile model of the eye 30 can be used to determine the angle at which the laser beam is incident on the eye 30. For example, an abbreviated form of a model eye, which is known for a long time as a classic surface-profile model of a typical eye, may be used. See, for example, "Oshima, H. Optical mechanism of eyes. Journal of the Japan Society of Precision Engineering, 27-11."

The line-of-sight detection device 10 according to the present embodiment calculates and determines in advance, as the incident angle that the laser beam forms with the eye 30, the incident angle at which the laser beam is incident on the PSD 3 in the center of the photo-sensing surface, using, for example, a ray-tracing algorithm.

A method of calculating the degree of inclination of the eye 30 by the estimation unit 118 is described in further detail. The estimation unit 118 according to the present embodiment calculates the degree of inclination of the eye 30, which is equivalent to the line-of-vision direction 34, based on the information about the size or shape of the eye 30 or the parameters such as the position of the rotation center 58 of the eye 30.

Figure 5:
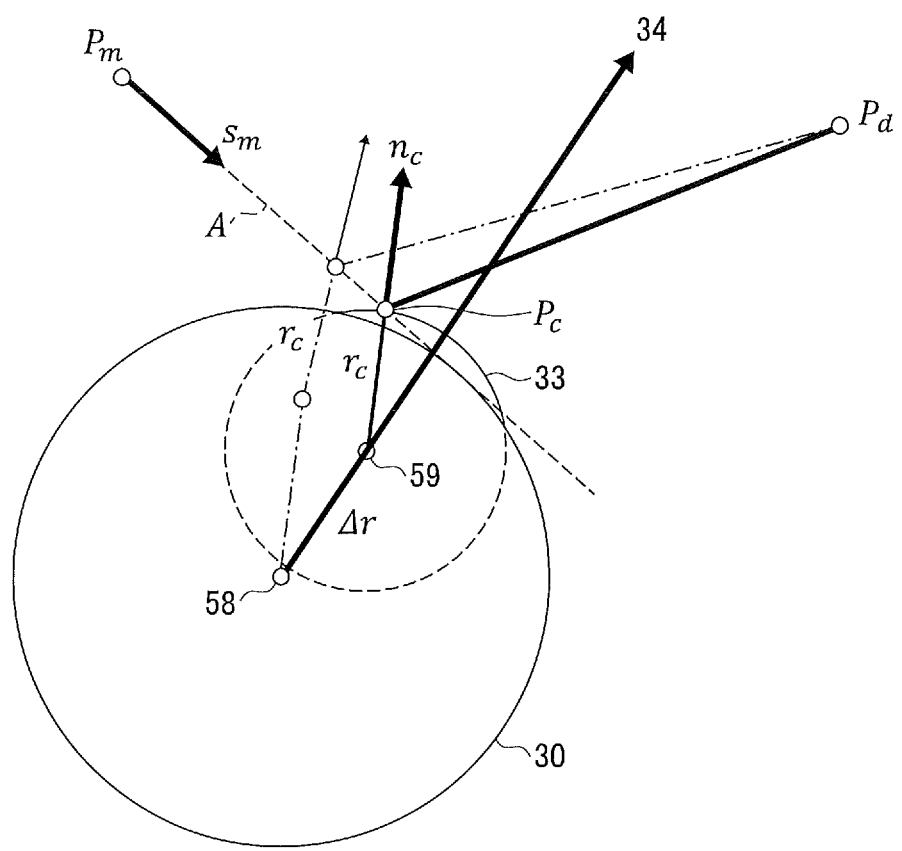
FIG. 5 is a diagram illustrating a method of determining the direction in which the eye is inclined based on the position of a PSD on which the light is incident, according to an embodiment of the present disclosure.

FIG. 5 is a diagram illustrating how to determine the direction in which the eye 30 is inclined, based on the position of the PSD 3 on which a laser beam is incident, according to the present embodiment.

In FIG. 5, a point of reflection $P_m$ of a concave mirror and a laser-beam vector $s \downarrow m$ are parameters given in advance by the line-of-sight detection device 10. Assuming that a point of reflection $P_c$ of a laser beam on the cornea 33 is on the extension of the laser-beam vector $s_m$ along the length A, a normal vector $n \downarrow c$ at the point of reflection $P_c$ of the laser beam can be determined based on the multiple pairs of coordinates of a PSD landing point $P_d$, the point of reflection $P \downarrow m$ of the concave mirror, and the point of reflection $P_c$ of the laser beam.

The radius of curvature R2 of the cornea 33 is given in advance as the parameters that indicates the shape of the eye 30, and a center of curvature 59 of the cornea 33 is uniquely determined based on the normal vector $n_c$. As the rotation center 58 of the eye 30 is given in advance, the distance Rd between the rotation center 58 of the eye 30 and the center of curvature 59 of the cornea 33 is determined.

The estimation unit 118 according to the present embodiment selects the length A such that the distance Rd obtained when the length A is assumed will be equal to the distance Δr between the center of curvature 59 of the cornea 33 and the rotation center 58 of the eye 30, which is given in advance as the parameters that indicates the shape of the eye 30. For example, the estimation unit 118 according to the present embodiment solves an equation given below to calculate a straight line connecting the rotation center 58 of the eye 30 to the center of curvature 59 of the cornea. In other words, the line-of-vision direction 34 of the eye 30 is obtained.

$$A = \arg_{min}(Rd - \Delta r)$$

In the above equation, the distance Rd is a function of the length A with reference to the center of curvature 59 of the cornea 33, and arg min is a mathematical symbol indicating that the length A is selected so as to minimize the value in the parentheses. In FIG. 5, the reflected laser beam that is indicated by the dot-and-dash line indicates the optical path when the length A is not appropriately selected. Moreover, the dotted lines in bold indicate the distance between the point of reflection $P_c$ of the laser beam on the cornea 33 and the center of curvature 59 of the cornea 33, and the distance Rd between the center of curvature 59 of the cornea 33 and the rotation center 58 of the eye 30 is illustrated. In FIG. 5, the distance Rd between the center of curvature 59 of the cornea 33 and the rotation center 58 of the eye 30 does not match the distance Δr.

In the above embodiment of the present disclosure, the line-of-vision direction 34 is determined based on the methodology in which the length A is optimized. However, no limitation is intended thereby, and any other desired methods may be adopted. For example, the position on which the laser beam is incident, which is obtained by the PSD 3, may be approximated by polynomial approximation of the rotation angle of the eye 30, and the line-of-vision direction 34 of the eye 30 may be calculated based on an inverse arithmetic expression.

The storage unit 117 according to the present embodiment stores the incident angle that the laser beam forms with the eye 30 and an inverse arithmetic expression used to estimate the degree of inclination of the eye 30. The estimation unit 118 according to the present embodiment refers to the storage unit 117, and obtains an inverse arithmetic expression including the parameters. Then, the estimation unit 118 calculates the degree of inclination of the eye 30 based on the position of the laser beam reflected by the eye 30 and the obtained inverse arithmetic expression, to obtain the information about the line-of-vision direction.

The output unit 119 according to the present embodiment serves as an output unit that outputs the information about the line-of-vision direction, which is obtained by the estimation unit 118, to an external device or the like. Such an external device may be, for example, an eye tracking device, an optometric device, a retinal projection display device, and a head-mounted display (HMD).

The degree of inclination of the eye 30 and the changes in the position of the laser beam reflected by the eye 30 due to the degree of inclination of the eye 30 are described below with reference to FIG. 6 and FIG. 7.

Human eyes constantly perform unconscious movement called involuntary eye movement during fixation, and the line-of-vision direction constantly changes depending on the involuntary eye movement during fixation. Technically, the involuntary eye movement during fixation is classified into characteristic movements such as microsaccades, tremors, and drifts. However, no such classification is referred to or described in detail in the present disclosure, and the involuntary eye movement during fixation is regarded as a movement with certain statistical fluctuations.

Figure 6:
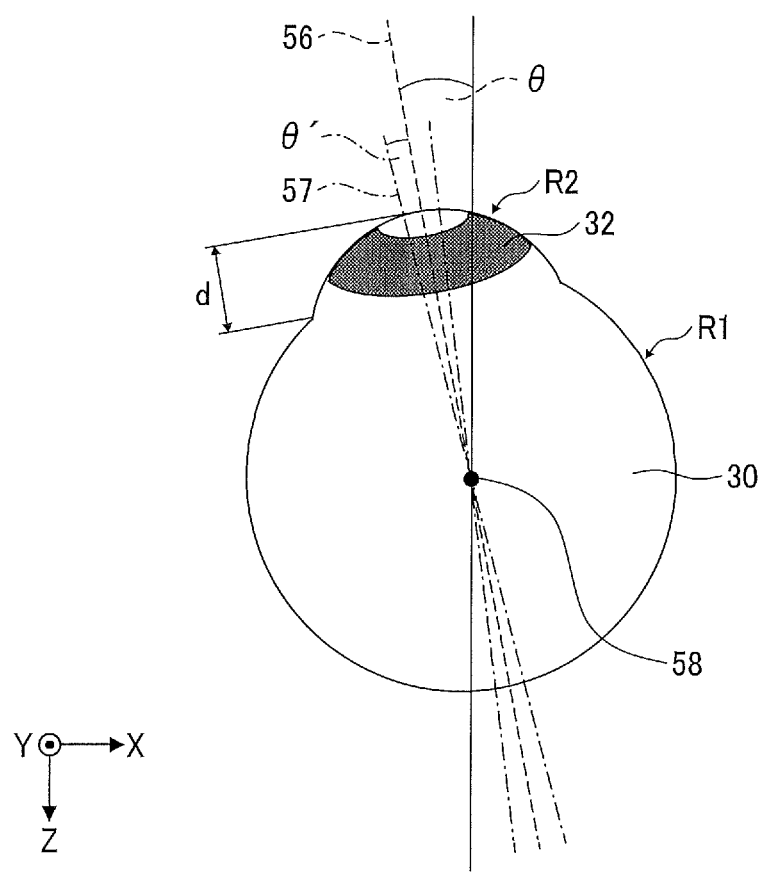
FIG. 6 is a diagram illustrating the relation between the line-of-vision direction of an eye and the involuntary eye movement during fixation, according to an embodiment of the present disclosure.

FIG. 6 is a diagram illustrating the relation between the line-of-vision direction of the eye 30 and the involuntary eye movement during fixation, according to the present embodiment.

The eye 30 rotates about the rotation center 58, and is inclined. When a person changes his/her line-of-sight, the eye 30 rotates and is inclined toward the line-of-vision direction 56 as indicated by a broken line in FIG. 6, and the eye 30 is inclined toward the line-of-vision direction 56 and the eye 30 repeatedly performs rotational movement around the line-of-vision direction 56 at a relatively narrow angle due to the involuntary eye movement during fixation.

In FIG. 6, a radius of curvature R1 indicates the radius of curvature of the eye 30, and a radius of curvature R2 indicates the radius of curvature of the cornea 33. Moreover, an amount of protrusion d indicates the amount of protrusion of the cornea 33 with respect to the eye 30.

A direction 57 of the involuntary eye movement during fixation is indicated by alternate long and short dashed lines in FIG. 6, and indicates a direction in which the eye 30 is inclined due to the involuntary eye movement during fixation. In the present embodiment described with reference to FIG. 6, the eye 30 is inclined toward the line-of-vision direction 56 at an angle θ with respect to the Z-axis as the line of sight of a human changes, and the eye 30 is inclined toward the direction 57 of the involuntary eye movement during fixation at an angle θ' with respect to the line-of-vision direction 56, in accordance with the involuntary eye movement during fixation.

Figure 7:
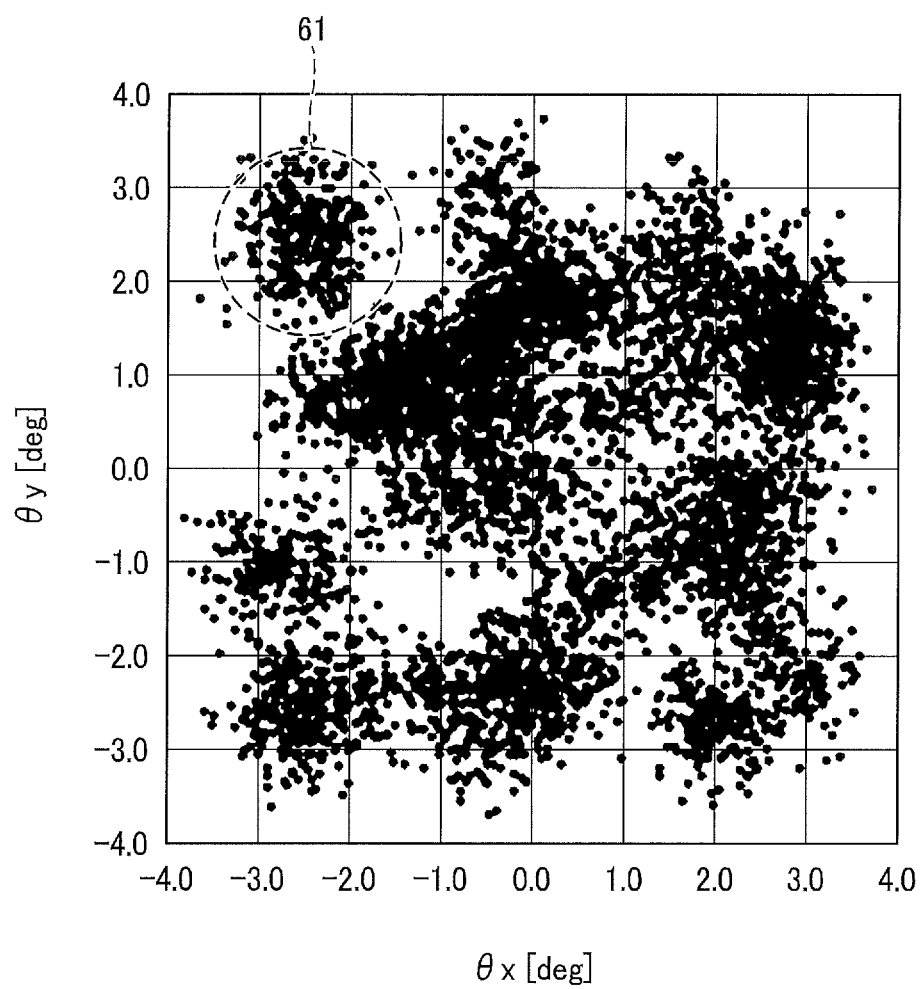
FIG. 7 is a diagram illustrating the results of simulation about the changes in the inclination of an eye, according to an embodiment of the present disclosure.

FIG. 7 is a diagram illustrating the results of simulation about the changes in the inclination of the eye 30, according to the present embodiment.

More specifically, FIG. 7 illustrates the inclination of the eye 30 in multiple directions with respect to the X-axis and the Y-axis.

In the simulation, it is assumed that the eye 30 randomly changes the line-of-vision direction by 100 points within an angular range of ±3°. It is assumed that the eye 30 stochastically changes the inclination by 100 points each time due to the involuntary eye movement during fixation in each one of the changes in the line-of-vision direction, in accordance with a normal distribution around the line-of-vision direction.

FIG. 7 illustrates a case where the line-of-vision direction changes by 50 points and the degree of inclination of the eye 30 changes by 100 points due to the involuntary eye movement during fixation in each one of the changes in the line-of-vision direction. The total number of plots in its entirety is as follows. 50×100=5000 (points)

For example, in a region 61 circled and indicated by a broken line, an angle θx that is a component of an angle θ of the line-of-vision direction in the X-axis direction is approximately −2.5 degrees, and an angle θy that is a component of an angle θ of the line-of-vision direction in the Y-axis direction is approximately 2.5 degrees. The inclination slightly changes around the line-of-vision direction due to the involuntary eye movement during fixation, and the inclinations are distributed around the line-of-vision direction. As described above, the eye 30 perform involuntary eye movement during fixation while changing the line-of-vision direction. As a result, the degree of inclination is changed as illustrated in FIG. 7.

Figure 8:
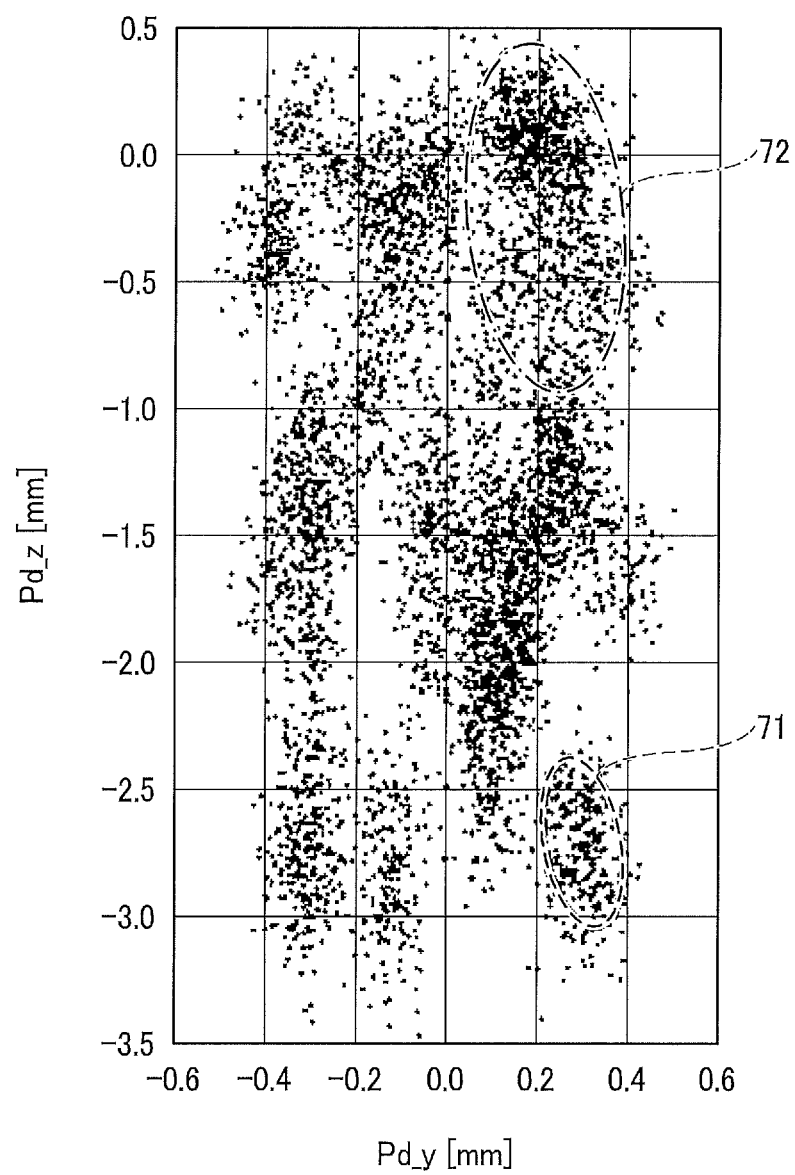
FIG. 8 is a diagram illustrating the results of simulation of the distribution of the positions on a PSD that a plurality of laser beams reach, according to an embodiment of the present disclosure.

FIG. 8 is a diagram illustrating the results of simulation of the distribution of the points at which the laser beams reflected by the eye 30 reach the photo-sensing surface of the PSD 3 when the eye 30 perform involuntary eye movement during fixation while changing the line-of-vision direction, according to the present embodiment.

In FIG. 8, a position Pd_y that is indicated in the horizontal axis indicates the position on the photo-sensing surface of the PSD 3 in the Y-axis direction, and a position Pd_z that is indicated in the vertical axis indicates the position on the photo-sensing surface of the PSD 3 in the Z-axis direction.

FIG. 8 illustrates the changes in the points at which the laser beams reflected by the eye 30 reach the photo-sensing surface of the PSD 3 when the eye 30 whose position is specified by the parameters is inclined due to the rotational movement as illustrated in FIG. 7. The positions on the PSD 3 that the laser beams reach are calculated based on the simulation using a ray-tracing algorithm. It is assumed that the components are arranged such that the laser beam is incident on the cornea 33 of the eye 30 at an incident angle of 60 degrees.

The parameters that are used in the present embodiment are as follows.

Radius R1 of Eye 30 (see FIG. 6): 13.12 millimeters (mm)
Radius of Curvature R2 of Cornea 33 of Eye 30 (see FIG. 6): 7.92 (mm)
Amount of Protrusion d of Cornea 33 of Eye 30 (see FIG. 6): 0.24 (mm)
Coordinates ($\Delta x$, $\Delta y$, $\Delta z$) of Rotation Center 58 of Eye 30 (see FIG. 6): (−21.46, 0.48, −17.37) (mm)

Note that the coordinates of the rotation center 58 of the eye 30 are the coordinates when it is assumed that the center of the photo-sensing surface of the PSD 3 is the point of origin.

As illustrated in FIG. 8, the position of the laser beam is distributed over a wide range on the photo-sensing surface of the PSD 3. Moreover, the distribution of the positions of the laser beams includes a plurality of clusters that are a set of the positions of multiple laser beams.

For example, a cluster 71 that is indicated by a broken line in FIG. 8 includes a set of plots that indicate the positions of a plurality of laser beams when the position Pd_z is approximately within range of −3.0 to −2.5 mm and the position Pd_y is approximately within range of 0.2 to 0.4 mm. The distribution of the positions of laser beam includes a plurality of clusters such as cluster 71.

Further, the width of change of the position of the laser beam in the cluster is different for each cluster. The variation width of the position in the cluster corresponds to the variation width of the inclination in the involuntary eye movement during fixation of the eye 30. The width of change can also be referred to as a width of fluctuation, and is hereinafter referred to as a width of fluctuation.

For example, in the cluster 72 placed in the normal direction of the Z axis with respect to the cluster 71, the width of fluctuation of the position of the laser beam increases in the Z-axis direction compared with the cluster 71. The normal direction of the Z axis corresponds to a direction shifting away from the eye 30.

The width of fluctuation of the cluster in the Z-axis direction is minimized near the point where the position Pd_z becomes 0, and the width of fluctuation of the cluster in the Z-axis direction increases toward each of the normal direction and negative direction in the Z-axis direction.

The width of fluctuation of the clusters in the Z-axis direction changes depending on the size or shape of the eye 30 or the position of the rotation center 58 of the eye 30. Accordingly, the above parameters can be extracted by extracting the amount of characteristic of the cluster caused by the involuntary eye movement during fixation in the distribution of the positions of the laser beams. In order to extract a cluster from a plurality of detection values, for example, a cluster analysis method for example may be adopted.

The position of the rotation center 58 of the eye 30 changes according to the position at which a person wears the line-of-sight detection device 10. When the position at which a device or apparatus is disposed deviates greatly, the position of the rotation center 58 greatly changes.

The correlation between the averages and standard deviations of a plurality of detection values that make up a cluster in the distribution of the positions of laser beams is described below with reference to FIG. 9A, FIG. 9B, and FIG. 9C.

Figure 9A:
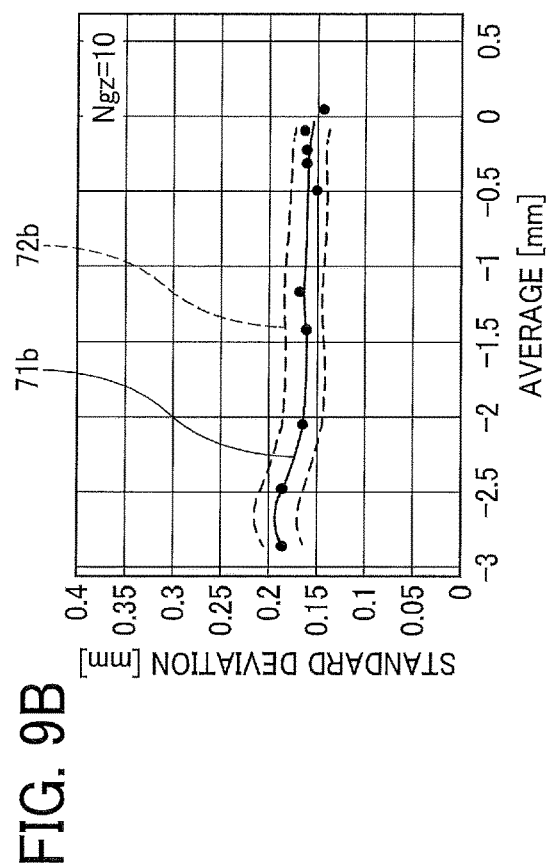
FIG. 9A, FIG. 9B, and FIG. 9C are diagrams illustrating the correlation between the averages of detection values and the standard deviations, according to an embodiment of the present disclosure.
Figure 9B:
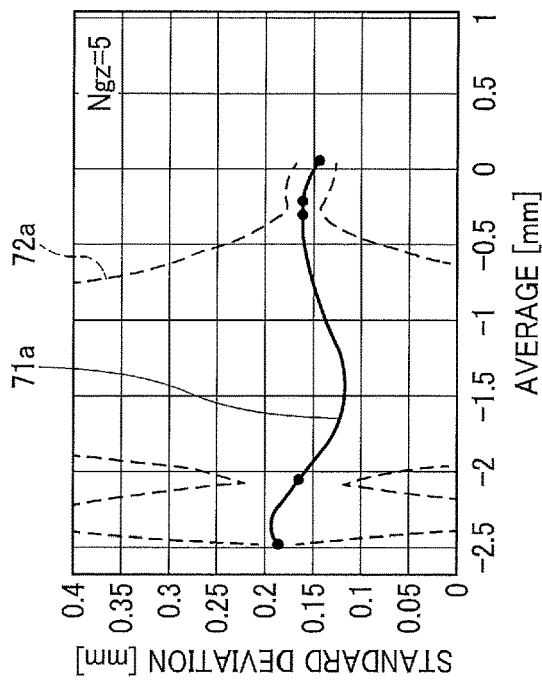
Figure 9C:
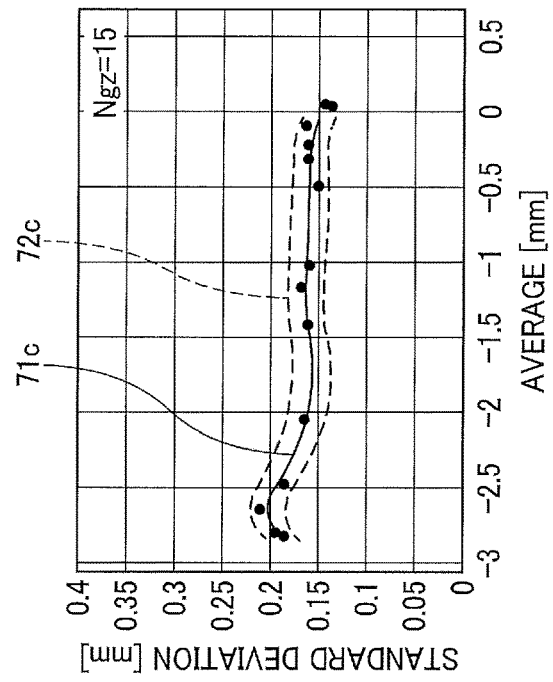

FIG. 9A, FIG. 9B, and FIG. 9C are diagrams illustrating the correlation between the averages of a plurality of detection values and the standard deviations, according to the present embodiment.

FIG. 9A illustrates a case in which the number of detection values is five, according to the present embodiment. FIG. 9B illustrates a case in which the number of detection values is ten, according to the present embodiment. FIG. 9C illustrates a case in which the number of detection values is fifteen, according to the present embodiment. Ngz in each graph indicates the number of detected values.

The horizontal axes in FIG. 9A, FIG. 9B, and FIG. 9C indicate an average value of detection values of a plurality of positions that make up a cluster, among the detection values of the positions of the laser beams reflected by the eye 30, which are obtained by the PSD 3. The vertical axes in FIG. 9A, FIG. 9B, and FIG. 9C indicate a standard deviation of detection values of a plurality of positions that make up a cluster, among the detection values of the positions of the laser beams reflected by the eye 30, which are obtained by the PSD 3. The average value corresponds to the center of gravity of the cluster, and the standard deviation corresponds to the width of fluctuation.

In FIG. 9A, FIG. 9B, and FIG. 9C, solid line graphs 71a, 71b, and 71c indicate polynomial approximation curves in the correlation between the average value and the standard deviation, and broken line graphs 72a, 72b, and 72c indicate the errors in generation in the above polynomial approximation curves. The error in generation of the polynomial approximate curve indicates the reliability of the polynomial approximate curve. As the error in generation is smaller, the reliability of the polynomial approximate curve increases, and the degree of correlation between the center of gravity of the cluster and the width of fluctuation increases.

As illustrated in FIG. 9A, FIG. 9B, and FIG. 9C, as the number of detection values increases, the error in generation in the polynomial approximation curve between the center of gravity of the cluster and the width of fluctuation decreases, and the reliability increases.

The polynomial approximation curve and the error in generation in each of FIG. 9A, FIG. 9B, and FIG. 9C are calculated based on Bayesian estimation. In the present embodiment, Bayesian estimation refers to a method of probabilistically or stochastically inferring an incident or event to be estimated from the observed incident or event based on the Bayesian estimation theory. As the Bayes estimation is adopted, the polynomial approximation curve and the error in generation can be calculated with high reliability even with a small number of detection values.

In the present embodiment, fa polynomial approximate curve that is approximated to a sixth-order polynomial is used. By setting the number of detection values to a value equal to or greater than ten, the error in generation becomes substantially constant, and the polynomial approximation curve that indicates the correlation between the center of gravity of the cluster and the width of fluctuation can be determined with high reliability.

When the parameter changes due to a change in the size or shape of the eye 30 or a shift in the mounting position of the line-of-sight detection device 10, the correlation curve between the position of the center of gravity of the cluster and the width of fluctuation becomes unstable. However, as the detected values are accumulated with no change, the correlation curve between the position of the center of gravity of the cluster and the width of fluctuation converges to a polynomial approximation curve where the relation between the position of the center of gravity of the cluster and the width of fluctuation differs. As a result, a polynomial approximation curve in which the changing unit 116 has reflected the changed parameters can be obtained.

Due to the configurations as described above, the polynomial approximation curve that indicates the correlation between the center of gravity of the cluster and the width of fluctuation and autonomously reflects the parameters such as the size or shape of the eyes 30 or the installation position when the values detected by the PSD 3 are obtained can be obtained.

In order to calculate the parameters based on the polynomial approximate curve of the position of the center of gravity of the cluster and the width of fluctuation, for example, geometrical optics may be used to obtain an approximate solution to the polynomial approximation curve that indicates the correlation between the center of gravity of the cluster and the width of fluctuation in view of the involuntary eye movement during fixation. Then, a conversion formula that indicates the corresponding relation between the coefficient of each member in the polynomial approximation curve and the parameters is obtained. By using the obtained conversion formula, the parameters can be calculated and obtained based on the position of the center of gravity of the cluster and the width of fluctuation.

Alternatively, a method may be adopted in which analysis of multiple variances such as canonical correlation analysis is used to obtain a conversion formula that indicates the corresponding relation between the coefficient of each member in the polynomial approximation curve and the parameters. By using the obtained conversion formula, the parameters can be calculated and obtained based on the position of the center of gravity of the cluster and the width of fluctuation.

In such an alternative method, the parameters as well as the coefficients of the polynomial correlation curve between the position of the center of gravity of a cluster and the standard deviation can be expressed by the canonical correlation analysis. Known technologies may be applied to the canonical correlation analysis.

The coefficients of the polynomial expression and the ocular parameters are each regarded as a vector and linearly transformed. A linear transformation matrix that maximizes the rate of correlation of each vector after linear transformation is obtained. In the present embodiment, each coefficient of the sixth-order polynomial is regarded as a vector, and each ocular parameter is also regarded as a vector. A linear transform matrix that maximizes the correlation coefficient of the transformed matrix when each vector is linearly transformed is obtained. Such a linear transformation matrix is used to estimate a vector on one side based on another vector on the other side. When the linear transformation is performed, the numbers of parameters or elements are matched to each other.

In the present embodiment, the data of the center of gravity of involuntary eye movement during fixation and the width of fluctuation are sequentially used as materials for the estimation based on the Bayesian estimation. Due to such a configuration, even if the data size is not so large, the estimation curve gradually converges as desired. The estimation accuracy of a sixth-order polynomial expression that is obtained based on Bayesian estimation improves every time the data of the center of gravity of involuntary eye movement during fixation and the width of fluctuation are added.

The data of the relation between the position of the center of gravity of the involuntary eye movement during fixation during fixation and the width of fluctuation and the ocular parameters is collected in advance based on simulation, and such obtained data is used as learnt data to extract a conversion formula used for the involuntary eye movement during fixation during fixation and the ocular parameters. Using the obtained conversion formula, the ocular parameters can be estimated from the data of the involuntary eye movement during fixation when the ocular parameters are unknown.

Figure 10:
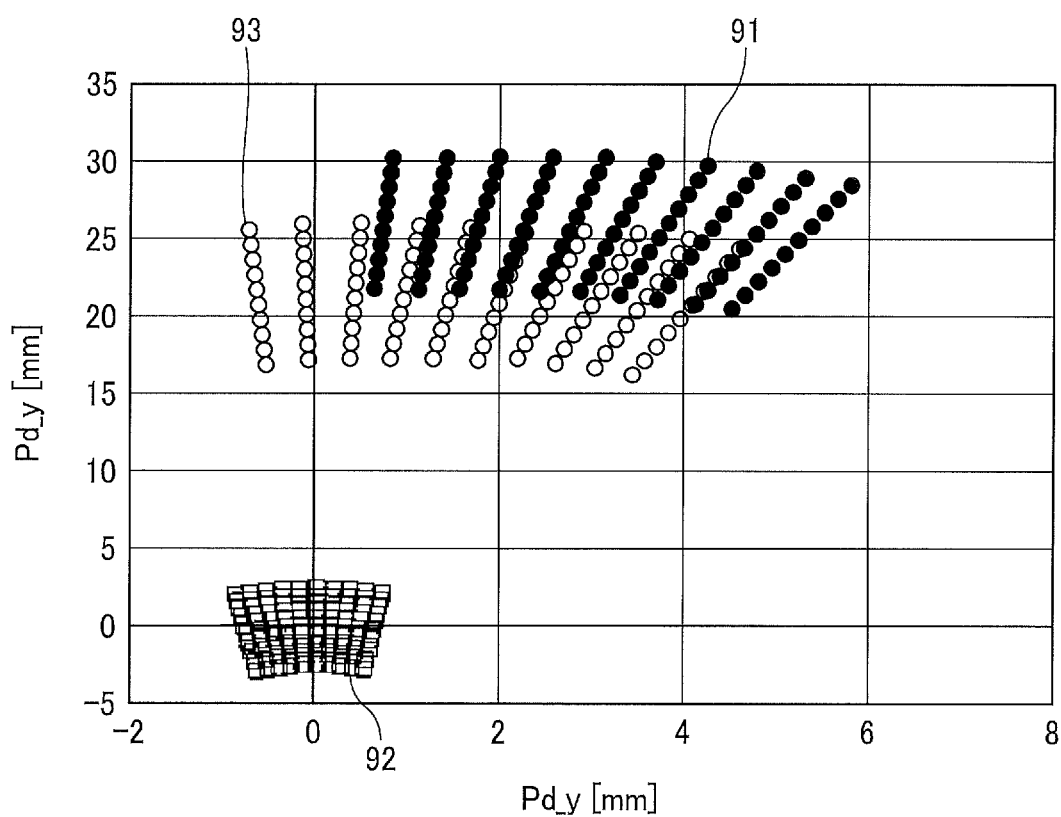
FIG. 10 is a diagram illustrating the effects of changing parameters, according to an embodiment of the present disclosure.

FIG. 10 is a diagram illustrating the effects of changing the parameters, according to the present embodiment.

More specifically, FIG. 10 illustrates the results of estimating the position on the photo-sensing surface of the PSD 3 at which the laser beam reflected by the eye 30 is incident when the eye 30 is inclined from −5.0 degrees to 4.0 degrees in increments of 1.0 degree around the X-axis and the Y-axis. The estimation in the present embodiment is performed by simulation.

A plurality of plots 91 that are indicated by black dotes in FIG. 10 indicate the positions on which the laser beams are incident that are obtained when predetermined parameters are used. The plots 91 can be referred to as a true values of the positions on which the laser beams are incident.

A plurality of plots 92 that are indicated by rectangles indicate the positions on which the laser beams are incident that are obtained when typical or average parameters are used. A plurality of plots 93 that are indicated by open circles in FIG. 10 indicate the positions on which the laser beams are incident that are obtained after the changing unit 116 has changed the parameters, based on the relation between the position of the center of gravity of the cluster and the width of fluctuation, which varies depending on the involuntary eye movement during fixation. A plurality of plots that indicates the positions on which the laser beams are incident are collectively be referred to as the plots 91, the plots 92, and the plots 93.

As illustrated in FIG. 10, compared with the plot 92, a plot 93 for which the changed parameters are used has values closer to the true values of the plot 91. As the parameters are changed, the estimation error in the position on the photo-sensing surface of the PSD 3 at which the laser beam reflected by the eye 30 is incident can be reduced. This indicates that the detection error of the line-of-vision direction by the line-of-sight detection device 10 is reduced. In particular, the detection error in the line-of-vision direction is reduced from 25.74 [mm] to 4.48 [mm] on the average of each plot.

Figure 11:
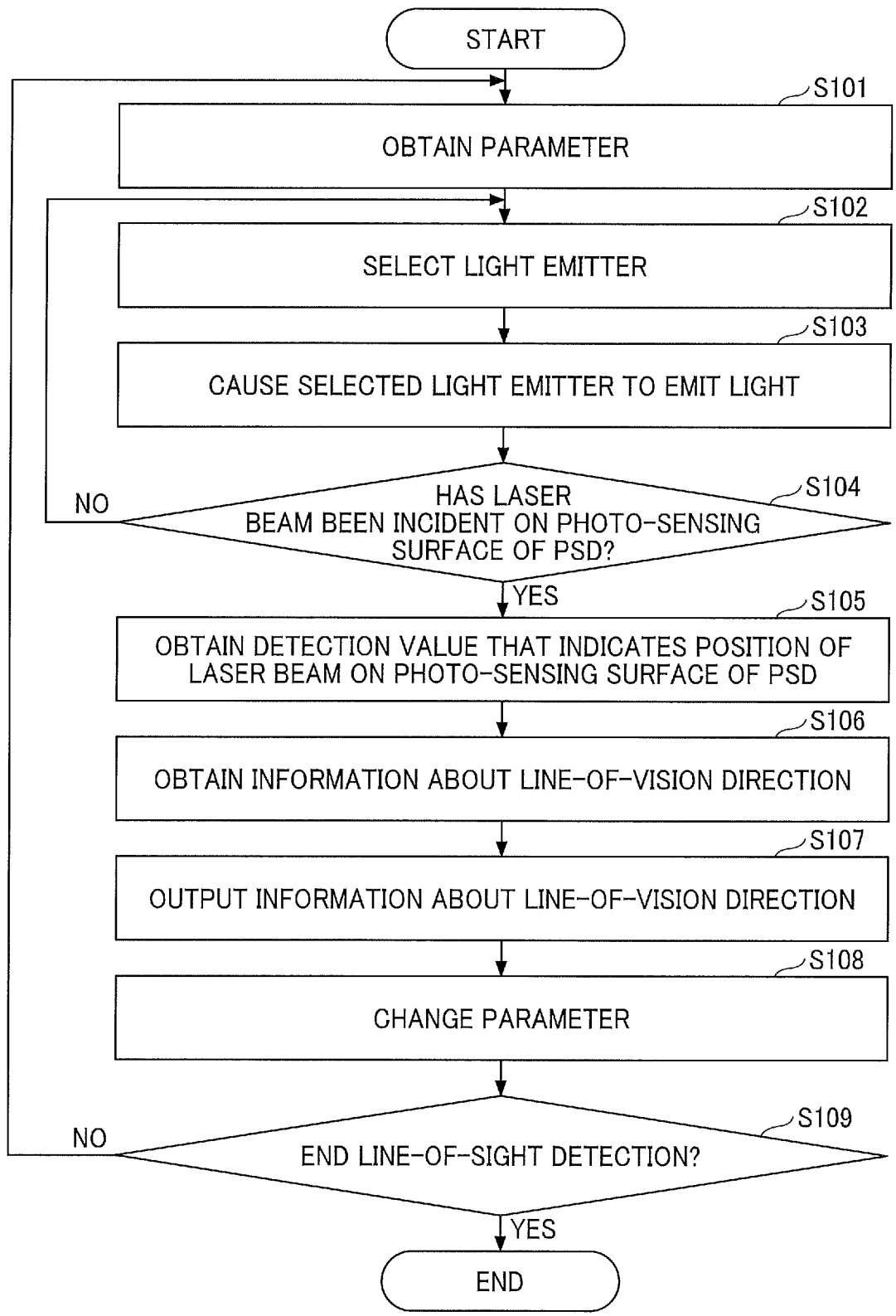
FIG. 11 is a flowchart of the processes performed by a line-of-sight detection device, according to the first embodiment of the present disclosure.

FIG. 11 is a flowchart of the processes performed by the line-of-sight detection device 10, according to the present embodiment.

FIG. 11 is a flowchart of the processes triggered by the line-of-sight detection performed by the line-of-sight detection device 10, according to the present embodiment.

Firstly, in a step S101, the estimation unit 118 according to the present embodiment refers to the storage unit 117 to obtain the information about the parameters stored in the storage unit 117.

Subsequently, in a step S102, the light emission controller 111 according to the present embodiment selects one of the multiple light emitters that the VCSEL 1 has.

Subsequently, in a step S103, the light emission controller 111 causes the selected light emitter to emit light.

Subsequently, in a step S104, the determining unit 112 according to the present embodiment receives the signals detected by the PSD 3, and determines whether the laser beam reflected by the eye 30 has already been incident on the photo-sensing surface of the PSD 3.

When it is determined that the light is not incident in the step S104 ("NO" in the step S104), the processes in the following steps of the step S102 are performed again.

On the other hand, when it is determined that the light is incident in the step S104 ("YES" in the step S104), in a step S105, the acquisition unit 113 performs analog-to-digital (A/D) conversion on the analog voltage signal that is detected by the PSD 3 and then input through the determining unit 112, to obtain, as a detection value, a digital voltage signal that indicates the position of a laser beam on the photo-sensing surface of the PSD 3.

Subsequently, in a step S106, the estimation unit 118 calculates the degree of inclination of the eye 30 based on the position of the laser beam reflected by the eye 30 and the parameters stored in the storage unit 117, to obtain information about the line-of-vision direction.

Subsequently, in a step S107, the output unit 119 according to the present embodiment outputs the information about the line-of-vision direction, which is obtained by the estimation unit 118, to an external device.

Subsequently, in a step S108, the extraction unit 115 and the changing unit 116 change the parameters in a cooperative manner. This changing operation will be described later in detail with reference to FIG. 12.

Subsequently, in a step S109, the processor 100 according to the present embodiment determines whether or not to end the line-of-sight detection. When it is determined that the line-of-sight detection is to be ended, the line-of-sight detection device 10 ends the operation. On the other hand, when it is determined that the line-of-sight detection is not to be ended, the line-of-sight detection device 10 performs the processes in the following steps of the step S101 again.

In this manner, the line-of-sight detection device 10 can detect the line-of-vision direction of the person wearing the spectacle-shaped support on which the line-of-sight detection device 10 is mounted.

In the present embodiment described with reference to FIG. 11, the line-of-sight detection device 10 changes the parameters in the step S108 after the information about the line-of-vision direction is output in the step S107. However, the order in which these processes are performed is not limited to this order. After the laser beam is incident on the photo-sensing surface of the PSD 3, for example, the line-of-sight detection device 10 may change the parameters in any order, or may change the parameters a plurality of times.

For example, the parameters may be changed before the estimation unit 118 obtains the information about the line-of-vision direction in the step S106, or the parameters may be changed a plurality of times between the step S105 and the step S109.

In the present embodiment, the change of the parameters and the detection of the line-of-vision direction are not performed in parallel, but the change of the parameters and the detection of the line-of-vision direction are performed at different timings. In other words, for example, the output unit 119 outputs the information about the line-of-vision direction at a first timing, and the changing unit 116 changes the parameters at a second timing different from the first timing. The timings at which the processes in the steps S105 to S107 are performed are an example of the first timing, and the timing at which the processes in the steps S108 is performed is an example of the second timing.

Figure 12:
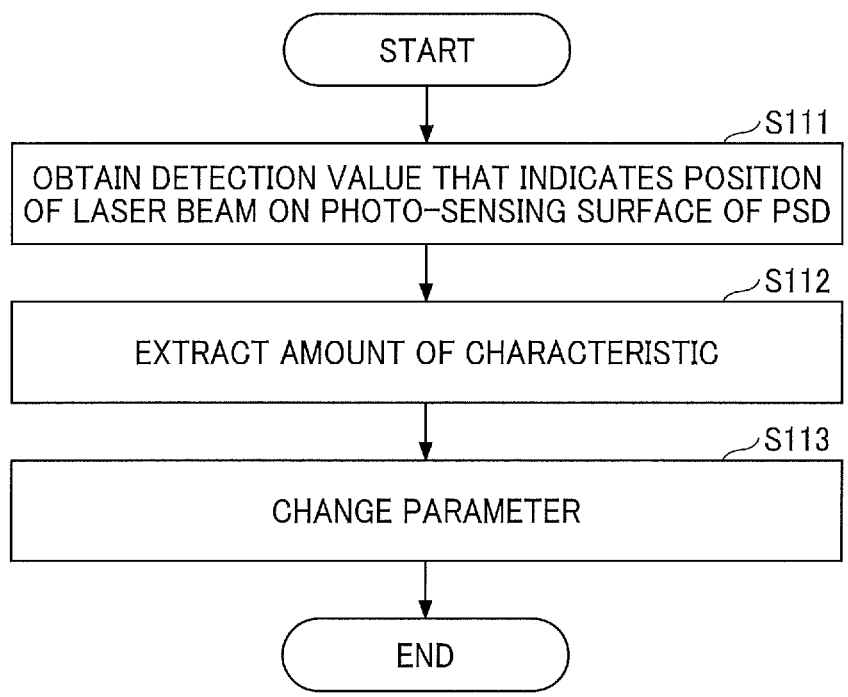
FIG. 12 is a flowchart of the changing processes performed by a line-of-sight detection device according to the first embodiment of the present disclosure.

FIG. 12 is a flowchart of the processes triggered by the changes of the parameters performed by the line-of-sight detection device 10, according to the present embodiment.

Firstly, in a step S111, the acquisition unit 113 according to the present embodiment performs A/D conversion on the analog voltage signals that are detected by the PSD 3 and then are input through the determining unit 112, to obtain, as a detection value, a digital voltage signal that indicates the position of a laser beam on the photo-sensing surface of the PSD 3.

Subsequently, in a step S112, the extraction unit 115 refers to the multiple detection values stored in the storage unit 114, and extracts the amounts of characteristic that indicates the characteristics of involuntary eye movement during fixation based on the calculated position of the center of gravity of the detection values making up the cluster and the width of fluctuation. The extraction unit 115 outputs the extracted data indicating the amount of characteristic to the changing unit 116.

Subsequently, in a step S113, the changing unit 116 according to the present embodiment changes the parameters stored in the storage unit 117 based on the amount of characteristic input from the extraction unit 115.

In this manner, the line-of-sight detection device 10 can change the parameters stored in the storage unit 117.

Some advantageous effects of the line-of-sight detection device 10 are described below.

Currently, technologies and products related to virtual reality (VR) and augmented reality (AR) attracts a lot of attention. In particular, the AR technology is expected to be applied to the industrial field as means for displaying digital information in a real space. In view of the fact that most of cognitive information is obtained from vision, a person who utilizes the AR technology performs actions (work). An optical device such as a glasses-type video display device that can be used in an environment has been developed.

As such a glasses-type image display device, retinal projection display devices that adopt a retinal drawing method and use a laser beam to draw an image directly on a human retina are known in the art. According to the retinal drawing method, a focus-free image can be superimposed on the information to be visually recognized As a result, the digital information can be displayed on the human retina while the viewpoint is on the external environment, and can be recognized by a human.

In the retinal projection display device that uses laser beams, due to the limitation on the size of the cornea and the pupil, there are some cases in which vignetting occurs to a laser beam on, for example, the cornea or the outer regions of the pupil under behavioral or operational environments involving eye motion and a predetermined image cannot be drawn at a predetermined position.

In order to handle such a situation, some technologies or configurations are proposed in which the laser beam is reflected by a micro-electromechanical systems (MEMS)

mirror to scan the surface of the eye and the position of the cornea of the eye is detected based on the signal detected by the laser beam reflected by the eye.

For example, mechanisms to irradiate an eye with a laser beam and detect the movement of the eye based on the laser beam reflected by the eye are known in the art.

However, in the conventional configuration, when the light reflected by the object such as the eye is largely deviated, the parameters such as the size or shape of the eye used to detect the corneal position of the eye or the movement of the eye, or the rotation center position of the eye are largely changed from a predetermined value, so that the detection error may be increased.

In the embodiments of the present disclosure, an object such as the eye 30 is irradiated with a laser beam or light, and the position of the laser beam that is reflected by the eye 30 is detected. As a result, the data about the inclination of the object, i.e., the data about the line-of-vision direction, that is obtained based on the position of the light and prescribed parameters is output. Then, the above parameters are changed based on the position of the laser beam reflected by the eye 30.

For example, the above parameters are changed based on the center of gravity of the detection values making up the cluster caused due to the involuntary eye movement during fixation of the eye 30 and the width of fluctuation or the width of change in the detection values making up the cluster. The position of the laser beam or light that is reflected by the eye changes in a distribution that varies depending on the characteristics of the involuntary eye movement during fixation, and the characteristic of the involuntary eye movement during fixation varies depending on, for example, variations among individuals in the size or shape of the eye and the positional displacements in the position at which the optical device such as the line-of-sight detection device is disposed.

In order to handle such a situation, the amounts of characteristic that indicates the characteristics of involuntary eye movement during fixation is extracted based on the position of the center of gravity of the detection values making up the cluster and the width of fluctuation, and the parameters (R1, R2, and d) are changed based on the extracted amount of characteristic. Accordingly, the influence of, for example, a deviation in the size or shape of the eye 30 and a deviation in the installation position of the line-of-sight detection device 10 can be compensated for. As a result, the detection error can be reduced even when the light reflected by the eye 30 deviates significantly.

In the present embodiment, for example, the output unit 119 outputs the information about the line-of-vision direction at a first timing, and the changing unit 116 changes the parameters at a second timing different from the first timing. As a result, the detection of the line-of-vision direction and the change of the parameters can be performed by a single PSD 3 that serves as a detector, and the configuration of the line-of-sight detection device 10 can be simplified.

The line-of-sight detection device 10 may include a plurality of PSDs 3, and may use the multiple PSDs 3 to perform both the detection of the line-of-vision direction and the change of the parameters in parallel.

The changing unit 116 according to the present embodiment repeatedly changes the parameters. For example, when the spectacle-shaped supporting structure is displaced and the position of the line-of-sight detection device 10 is suddenly or abruptly displaced while the spectacle-shaped supporting structure including the line-of-sight detection device 10 is being installed, the positional displacement of the line-of-sight detection device 10 cannot be compensated for in a configuration in which the parameters are changed only once. As the parameters are repeatedly changed, it is possible to handle a sudden or abrupt positional displacement of the line-of-sight detection device 10. The cycle of repetition may be a constant cycle or may be a cycle that changes at random.

In the present embodiment, the changing unit 116 changes the parameter based on the estimation value obtained by Bayesian estimation based on the detection value of the position of the laser beam. As the Bayesian estimation is adopted, the polynomial approximation curve and the error in generation can be calculated with high reliability even with a small number of detection values. Moreover, the parameters may be changed to more accurate parameters to further reduce the detection error.

Second Embodiment

A retinal projection display device 50 according to a second embodiment of the present disclosure is described below. In view of the first embodiment of the present disclosure as described above, like reference signs denote like elements, and redundant description may be omitted where appropriate.

Figure 13:
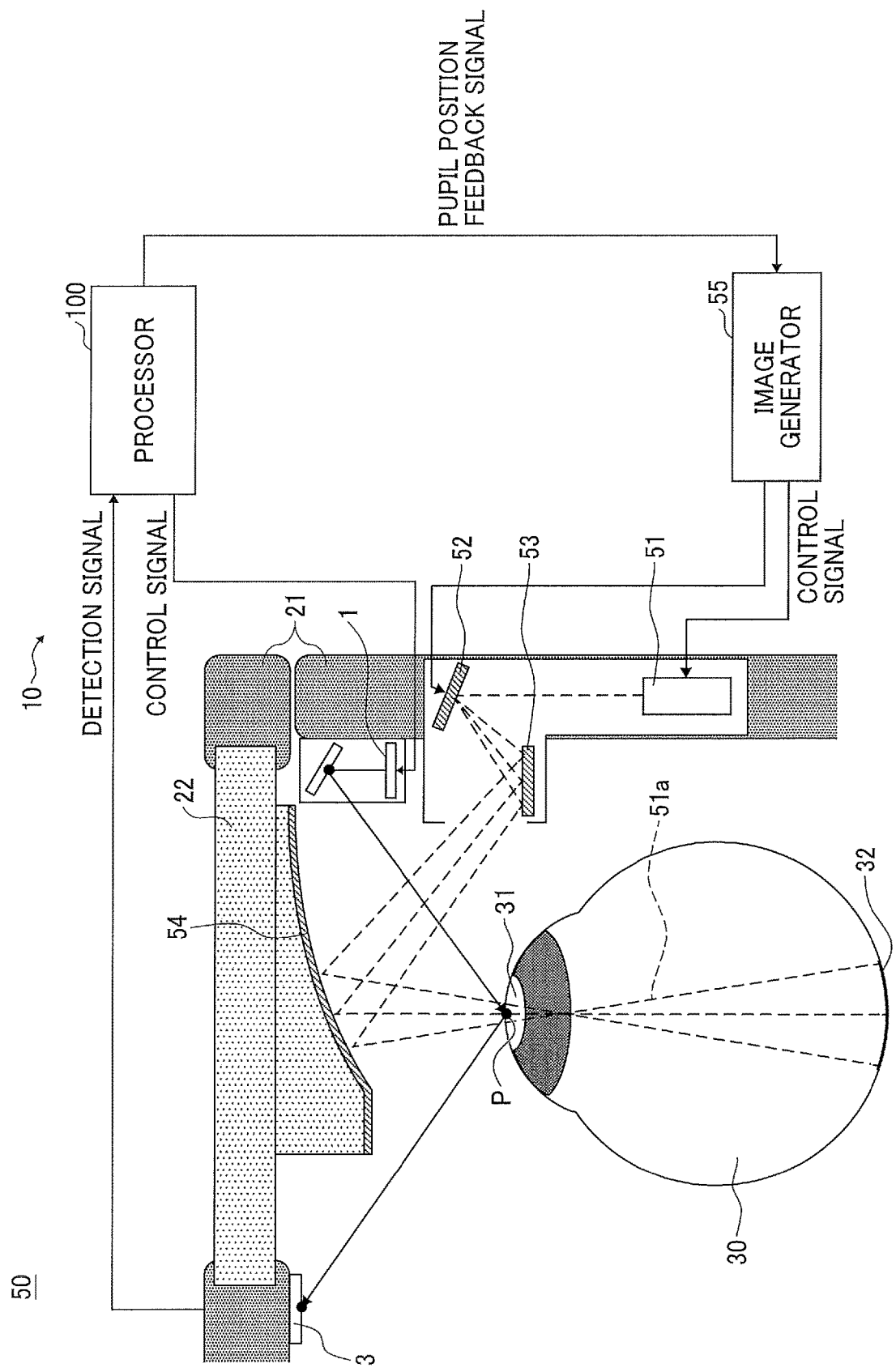
FIG. 13 is a diagram illustrating a configuration of a retinal projection display device according to a second embodiment of the present disclosure.

FIG. 13 is a diagram illustrating a configuration of the retinal projection display device 50 according to the second embodiment of the present disclosure.

As illustrated in FIG. 13, the retinal projection display device 50 includes a red, green, and blue (RGB) laser beam source 51, a scanning mirror 52, a plane mirror 53, a half mirror 54, an image generator 55, and the line-of-sight detection device 10 according to the first embodiment as described above.

The RGB laser beam source 51 according to the present embodiment temporally modulates the laser beam of three colors of RGB, and outputs the modulated laser beam. The scanning mirror 52 according to the present embodiment two-dimensionally scans the light emitted from the RGB laser beam source 51. The scanning mirror 52 is, for example, a micro-electromechanical systems (MEMS) mirror.

However, the scanning mirror 52 is not limited to the MEMS mirror, and may be a polygon mirror, a galvano mirror, for example as long as it has a reflection unit that scans light. The MEMS mirror is advantageous in terms of reduction in size and reduction in weight. For example, a method of driving a MEMS mirror may be any desired method including an electrostatic method, a piezoelectric method, and an electromagnetic method.

The plane mirror 53 reflects the scanning light reflected by the scanning mirror 52 toward the half mirror 54. The half mirror 54 transmits some of the incident light, and reflects different some of the incident light toward the eye 30. The half mirror 54 that has a concave curved surface converges the reflected light near the pupil 31 of the eye 30, and forms an image approximately at a position of the retina 32. As a result, an image that is formed by the scanning light is projected onto the retina 32.

A light 51a that is indicated by a broken line in FIG. 13 is indicates the light used to form an image on the retina 32. The half mirror 54 does not have to have a one-to-one relation in the radiation intensity of light between the reflected light and transmitted light.

The line-of-sight detection device 10 detects a line-of-vision direction that changes depending on the eye motion, and transmits a feedback signal indicating the information about the line-of-vision direction to the image generator 55.

The image generator 55 according to the present embodiment has a function to control the deflection angle of the scanning mirror 52 and a function to control the light emission of the RGB laser beam source 51. The image generator 55 receives a feedback signal indicating the line-of-vision direction from the line-of-sight detection device 10, and controls the deflection angle of the scanning mirror 52 and the light emission of the RGB laser beam source 51 according to the line-of-vision direction. Moreover, the image generator 55 rewrites the angle of projection of the image or the image data. Due to such a configuration, an image that reflects the results of eye tracking, which indicate the changes in line-of-vision direction caused by eye motion, can be formed on the retina 32.

In the above embodiment, a configuration in which the retinal projection display device 50 is a head-mounted display that is a wearable device is described by way of example. However, the retinal projection display device 50 that is implemented as a head-mounted display is not limited to a device directly worn on a human head, but may be a device indirectly worn on the human head having a member such as a holding part therebetween. For example, a binocular retinal projection display device that includes a pair of retinal projection display devices 50 for both the right and left eyes may be adopted.

The above-described embodiments are illustrative and do not limit the present disclosure. Thus, numerous additional modifications and variations are possible in light of the above teachings. For example, elements and/or features of different illustrative embodiments may be combined with each other and/or substituted for each other within the scope of the present disclosure.

For example, in the above-described embodiments of the present disclosure, the device that detects the degree of inclination of the eye 30 serves as an optical device. However, no limitation is indicated thereby. For example, an optical device may be mounted on a robot hand, and the degree of inclination of the robot hand that is an example of the object may be detected. In such cases, unique parameters are used to estimate the degree of inclination of the robot hand. When the robot hand exerts micro-vibration for tracking or the like, such micro-vibration can be handled in a similar manner to the involuntary eye movement during fixation, and the amount of characteristic of the cluster at the position of the laser beam can be extracted based on the micro-vibration. The extracted amounts of characteristic of the cluster can be used to change the parameters.

For example, the information about the line-of-vision direction that is detected by the line-of-sight detection device 10 can be used for the eye tracking in an input device of an electronic device. As a result, robust eye tracking can be implemented on, for example, the size or shape of the eye and the displacement of the line-of-sight detection device 10.

Such a configuration can also be applied to an optometric device that has a function to detect the degree of inclination of an eye and the position a pupil or cornea. The optometric device refers to an device capable of performing various kinds of examinations such as an eye test, an eye refractive power examination, an intraocular pressure examination, and an optical axial-length examination. The optometric device can perform non-contact examination on an eye, and includes a supporting unit configured to support the face of a subject, an optometric window, a display unit configured to stabilize the direction of the line of sight of an eye of a subject during the optometric examination, a controller, and a measurement unit. In order to increase the measurement precision of the measurement unit, a subject is requested to gaze at one point without moving the line of sight of an eye. More specifically, the subject is requested to fix his/her face to the supporting unit, and to gaze at an object displayed on the display unit through the optometry window. In so doing, an inclined-position detector for eyes of according to the embodiments of the present disclosure can be used to detect the inclined position of the eye. The inclined-position detector for eyes is arranged away from the measurement unit so as not to disturb measurement. The information about the inclined position or line-of-vision of the eye, which is obtained by the inclined-position detector of the eye, can be fed back to the controller, and measurement can be performed based on the information about the inclined position of the eye.

The embodiments of the present disclosure also include a method of detecting the degree of inclination of a three-dimensional object. For example, the method of detecting the degree of inclination of the three-dimensional object includes a step of irradiating an object with light, a step of detecting a position of the light reflected by the object, a step of outputting data about inclination of the object obtained based on the position of the light and prescribed parameters, and a step of changing the parameter based on the position of the light. With such a method of detecting the degree of inclination of the three-dimensional object, functions similar to those implemented by the above optical device can be implemented.

Embodiments of the present disclosure includes a method of detecting a line-of-sight. For example, such a method of detecting the line-of-sight includes a step of irradiating an object with light, a step of detecting a position of the light reflected by the object, a step of outputting data about inclination of the object obtained based on the position of the light and prescribed parameters, and a step of changing the parameter based on the position of the light. With such a method of detecting a line-of-sight, functions similar to those implemented by the above optical device can be implemented.

The numbers such as ordinal numbers and numerals that indicates quantity are all given by way of example to describe the technologies to implement the embodiments of the present disclosure, and no limitation is indicated to the numbers given in the above description. The description as to how the elements are related to each other, coupled to each other, or connected to each other are given by way of example to describe the technologies to implement the embodiments of the present disclosure, and how the elements are related to each other, coupled to each other, or connected to each other to implement the functionality in the present disclosure is not limited thereby.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

Any one of the above-described operations may be performed in various other ways, for example, in an order different from the one described above.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

What is claimed is:

1. An optical device comprising:
   a light source configured to irradiate an object with light;
   a detector having a photo-sensing surface, the detector configured to receive the light reflected by the object and detect a position of the reflected light on the photo-sensing surface thereof; and
   circuitry configured to
   output data of a degree of inclination of the object obtained based on the position of the light on the photo-sensing surface of the detector and a prescribed parameter, and
   change the prescribed parameter based on the position of the light on the photo-sensing surface of the detector,
   wherein the light source includes multiple light emitters,
   one of the multiple light emitters is selected to irradiate the object,
   the selected one of the multiple light emitters is changed to another one of the multiple light emitters when the light is not incident on the photo-sensing surface of the detector, and
   the changing is repeated until the light is incident on the photo-sensing surface of the detector.

2. The optical device according to claim 1, further comprising
   a storage unit configured to store a plurality of detection values of the position of the light on the photo-sensing surface of the detector,
   wherein the circuitry is configured to change the prescribed parameter based on a position of a center of gravity of the plurality of detection values making up a cluster and a width of change in the plurality of detection values making up the cluster.

3. The optical device according to claim 1,
   wherein the circuitry is configured to output the data of the degree of inclination of the object at a first timing, and
   wherein the circuitry is configured to change the prescribed parameter at a second timing different from the first timing.

4. The optical device according to claim 3,
   wherein the circuitry is configured to change the prescribed parameter repeatedly.

5. The optical device according to claim 1,
   wherein the circuitry is configured to change the prescribed parameter based on an estimation value obtained by Bayesian estimation based on a detection value of the position of the light.

6. A line-of-sight detection device comprising
   the optical device according to claim 1.

7. The line-of-sight detection device according to claim 6, wherein the prescribed parameter is at least one of a shape of an eye on which line-of-sight detection is performed or a position of a center of rotation of the eye.

8. A retinal projection display device comprising
   the line-of-sight detection device according to claim 6.

9. A head-mounted display comprising
   the line-of-sight detection device according to claim 6.

10. An optometric device comprising
    the line-of-sight detection device according to claim 6.

11. A method of detecting inclination of a three-dimensional object, the method comprising:
    irradiating an object with light from a light source including multiple light emitters;
    detecting a position of the light reflected by the object using a detector having a photo-sensing surface, the position of the light being a position of the reflected light on the photo-sensing surface of the detector;
    outputting data of a degree of inclination of the object obtained based on the position of the light on the photo-sensing surface of the detector and a prescribed parameter; and
    changing the prescribed parameter based on the position of the light on the photo-sensing surface of the detector;
    selecting one of the multiple light emitters to irradiate the object;
    changing the selected one of the multiple light emitters to another one of the multiple light emitters when the light is not incident on the photo-sensing surface of the detector; and
    repeating the changing of the selected one of the multiple light emitters until the light is incident on the photo-sensing surface of the detector.

12. H method of detecting inclination of a three-dimensional object according to claim 11, wherein a line-of-sight is detected.

13. A optical device comprising:
    a light source configured to irradiate an object with light;
    a detector having a photo-sensing surface, the detector configured to receive the light reflected by the object and detect a position of the reflected light on the photo-sensing surface thereof;
    circuitry configured to
    output data of a degree of inclination of the object obtained based on the position of the light on the photo-sensing surface of the detector and a prescribed parameter, and
    change the prescribed parameter based on the position of the light on the photo-sensing surface of the detector; and
    a storage unit configured to store a plurality of detection values of the position of the light on the photo-sensing surface of the detector,
    wherein the circuitry is configured to change the prescribed parameter based on a distribution of the plurality of detection values on the photo-sensing surface of the detector.

14. The optical device according to claim 1,
    wherein the prescribed parameter is information used to obtain the degree of inclination of the object.

* * * * *